(12) United States Patent
Xu et al.

(10) Patent No.: US 10,709,370 B2
(45) Date of Patent: Jul. 14, 2020

(54) BIOLOGICAL FLUID SEPARATION DEVICE

(71) Applicant: Becton, Dickinson and Company, Franklin Lakes, NJ (US)

(72) Inventors: Qihua Xu, Cary, NC (US); Gonghao Wang, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/618,570

(22) Filed: Jun. 9, 2017

(65) Prior Publication Data

US 2017/0354362 A1 Dec. 14, 2017

Related U.S. Application Data

(60) Provisional application No. 62/347,816, filed on Jun. 9, 2016.

(51) Int. Cl.
*A61B 5/15* (2006.01)
*B01D 61/18* (2006.01)
(Continued)

(52) U.S. Cl.
CPC .. *A61B 5/150755* (2013.01); *A61B 5/150251* (2013.01); *B01D 61/18* (2013.01);
(Continued)

(58) Field of Classification Search
CPC .... B01D 63/08; B01D 63/087; B01D 63/088; B01D 63/085; B01D 69/06; B01D 71/50;
(Continued)

(56) References Cited

U.S. PATENT DOCUMENTS 4,066,554 A 1/1978 Guyer
4,343,705 A 8/1982 Legg
(Continued)

FOREIGN PATENT DOCUMENTS

EP 0403031 A2 12/1990
EP 0464707 A2 1/1992
(Continued)

OTHER PUBLICATIONS

Japanese Office Action issued in corresponding JP application No. 2017-564128 dated Nov. 13, 2018, pp. 5
(Continued)

*Primary Examiner* — Pranav N Patel
(74) *Attorney, Agent, or Firm* — Botos Churchill IP Law LLP

(57) ABSTRACT

A blood separation device adapted to receive a blood sample having a whole blood portion and a plasma portion is disclosed. The blood separation device includes a housing defining a first chamber, a second chamber, and a separation member disposed therebetween. The blood separation device also includes an actuator, wherein actuation of the actuator draws the blood sample into the first chamber and the separation member is adapted to allow the plasma portion to pass through the separation member to the second chamber. The blood separation device matches the plasma chamber volume, the blood chamber volume, and the applied single pressure source so that the correct transmembrane pressure and shear rate is obtained.

32 Claims, 32 Drawing Sheets

(51) Int. Cl.
 *G01N 33/49* (2006.01)
 *B01L 3/00* (2006.01)
(52) U.S. Cl.
 CPC ...... *B01L 3/502761* (2013.01); *G01N 33/491* (2013.01); *B01D 2325/02* (2013.01); *B01L 3/502715* (2013.01); *B01L 2300/0681* (2013.01); *B01L 2300/0816* (2013.01); *B01L 2300/0877* (2013.01); *B01L 2300/0883* (2013.01); *B01L 2300/0887* (2013.01); *B01L 2400/049* (2013.01); *B01L 2400/0487* (2013.01)
(58) Field of Classification Search
 CPC .......... B01D 2313/086; B01D 29/0004; B01D 29/0095; B01D 29/01; B01D 29/05; A61M 1/16; A61M 1/1631; A61M 1/34; A61M 2205/3331; A61M 2205/3334; A61M 2205/3355; A61M 2202/0413; A61M 2202/0415
 See application file for complete search history.

(56) References Cited

U.S. PATENT DOCUMENTS

| | | | |
|---|---|---|---|
| 4,740,313 A | 4/1988 | Schoendorfer et al. | |
| 4,769,150 A | 9/1988 | Ramstack | |
| 4,871,462 A | 10/1989 | Fischel et al. | |
| 5,034,135 A | 7/1991 | Fischel | |
| 5,100,376 A | 3/1992 | Blake | |
| 5,922,210 A | 7/1999 | Brody | |
| 6,010,627 A * | 1/2000 | Hood, III | A61K 35/14 210/321.6 |
| 6,153,104 A * | 11/2000 | Robertson | B01L 3/50255 210/406 |
| 8,889,071 B2 | 11/2014 | Aota et al. | |
| 2004/0251214 A1 | 12/2004 | Adams | |
| 2005/0261642 A1 * | 11/2005 | Weston | A61M 1/0088 604/313 |
| 2007/0151924 A1 | 7/2007 | Mir et al. | |
| 2008/0272283 A1 | 11/2008 | Feldsine et al. | |
| 2010/0285573 A1 | 11/2010 | Leck | |
| 2011/0155667 A1 * | 6/2011 | Charest | A61M 1/16 210/651 |
| 2012/0291867 A1 * | 11/2012 | Gassman | A61M 1/02 137/1 |
| 2013/0015119 A1 | 1/2013 | Pugh et al. | |
| 2013/0334139 A1 | 12/2013 | Blickhan | |
| 2014/0042094 A1 * | 2/2014 | Montagu | B01D 61/22 210/650 |
| 2014/0217027 A1 * | 8/2014 | Meyer | A61M 1/1601 210/646 |
| 2014/0305196 A1 | 10/2014 | Ellis et al. | |
| 2014/0308167 A1 | 10/2014 | Fletcher et al. | |
| 2014/0309556 A1 | 10/2014 | Fletcher et al. | |
| 2015/0060363 A1 | 3/2015 | Kusters et al. | |
| 2016/0074569 A1 | 3/2016 | Schuetz | |

FOREIGN PATENT DOCUMENTS

| | | | |
|---|---|---|---|
| EP | 2842619 | A1 | 3/2015 |
| JP | S57104862 | A | 6/1982 |
| JP | 61172060 | S | 8/1986 |
| JP | HEI03247345 | | 11/1991 |
| JP | 2010237050 | A | 10/2003 |
| KR | 20020061895 | A | 7/2002 |
| WO | 19910001796 | A1 | 2/1991 |
| WO | 9614578 | A1 | 5/1996 |
| WO | 9624425 | A1 | 8/1996 |
| WO | 20000050157 | A1 | 8/2000 |
| WO | 2012125460 | A1 | 9/2012 |
| WO | 2014023765 | A2 | 2/2014 |
| WO | 20150014934 | A1 | 2/2015 |

OTHER PUBLICATIONS

Chinese Office Action received in 201780048849.8 dated Nov. 21, 2019, pp. 15.
International Search Report and Written Opinion for Application No. PCT/US2017/036747 dated Nov. 21, 2017.
ISR and Written Opinion for Application No. PCT/US2016/036209 dated Aug. 25, 2016.
Jaffrin My: Innovative Processes for Membrane Plasma Separation 11, Journal of Membrane Science, Elsevier BV, NL, vol. 44, No. 1, Jun. 1, 1989 (Jun. 1, 1989), pp. 115-129, XP000068839, ISSN: 0376-7388, DOI: 10.1016/S0376-7388(00)82344-3, pp. 123-124.
Japanese Official Notice of Rejection issued in corresponding JP application No. 2017-563527 dated Oct. 23, 2018.
Wang Z F et al: "Seamless joining of porous membrane with thermoplastic microfluidic devices", Microelectronic Engineering, vol. 110 , XP028673721, ISSN: 0167-9317, DOI: 10.1016/J.MEE.2013.02.074, pp. 386-391.

\* cited by examiner

| Prior Art Single Pass Device | Input Blood μL | Plasma Yield, μL | Time, mins |
|---|---|---|---|
| Zahn Design | 500 | 50 | 10 |

FIG. 5

PRIOR ART

| Device # | Input Vol. mL | Output Vol. μL | Hemoglobin mg/dL |
|---|---|---|---|
| 1 | 2.6 | 477.8 | |
| 2 | 2.2 | 331.2 | 12.9 |
| 3 | 2.8 | 376.2 | |
| 4 | 3 | 435.7 | |
| 5 | 3 | 331.9 | 8.4 |
| 6 | 3 | 416.1 | |
| 7 | 3 | 482.6 | |
| 8 | 3 | 335.1 | 12.6 |
| 9 | 3 | 475.3 | |
| Control | - | - | 3.8 |

FIG. 6

| | Input Whole Blood | Plasma Control | Plasma Sample 1 | Plasma Sample 2 | Plasma Sample 3 |
|---|---|---|---|---|---|
| WBC, $\times 10^3$ /μL | 4.5 | 0.1 | 0.1 | 0.0 | 0.1 |
| RBC, $\times 10^3$ /μL | 5.36 | 0.00 | 0.00 | 0.00 | 0.00 |
| PLT, $\times 10^3$ /μL | 131 | 0 | 0 | 0 | 0 |
| HCT, % | 46 | 0.0 | 0.0 | 0.0 | 0.0 |

FIG. 7

| Device # | Input Vol. mL | Output Vol. mL |
|---|---|---|
| 1 | 2.8 | 208.7 |
| 2 | 2.7 | 233.9 |
| 4 | 3 | 248.5 |
| 5 | 3 | 256.3 |
| 6 | 3 | 261.2 |
| 7 | 3 | 235.9 |
| 8 | 3 | 268.9 |

Plasma Yield vs. Plasma Storage Size

| 4 mL vacutainer/plasma storage size | 0.25 mL | 0.5 mL | 1.0 mL |
|---|---|---|---|
| Plasma yield, mL |  | 0.269 | 0.335 |
|  | 0.163 | 0.264 | 0.334 |
|  |  | 0.260 | 0.375 |

FIG. 12

| Vacutainer Size, 10 mL Heparin | 1 mL Plasma Collection Tube | | 4 mL Plasma Collection Tube | |
|---|---|---|---|---|
| | 12.5psi Vacutainer Pressure | 8psi Vacutainer Pressure | 12.5psi Vacutainer Pressure | 8psi Vacutainer Pressure |
| Yield, μl (with 3 mL input blood) of 55% Hematocrit) | 271.9 | 272.8 | 293.9 | 298.4 |
| | 250.4 | 243.3 | 360 | 312.6 |
| Separation Time, second | 56 | 105 | 72 | 137 |
| | 59 | 114 | 79 | 141 |
| Hemoglobin concentration, mg/dL | 39.8 | 0.8 | 14.8 | 1 |
| | 46.7 | 9.5 | 21.7 | 7 |

FIG. 18

| | Pressure (blood outlet), psi (Vacuum) | Pressure (plasma outlet), psi (Vacuum) | Pressure Difference, psi (Vacuum) | Yield, % Based on Available Plasma | Hemoglobin Concentration in Plasma mg/dL | Average Flow Rate, mL/min | Note |
|---|---|---|---|---|---|---|---|
| Exp 1 | 9 | 9 | 0 | 22.9 | 11 | 6.2 | |
| Exp 2 | 9 | 5 | -4 | 21.8 | 6.1 | 3.9 | |
| Exp 3 | 9 | 1 | -8 | 7.3 | 8.7 | 1.5 | difficult to control |
| Exp 4 | 7 | 5 | -2 | 18.8 | 4.8 | 4.3 | |
| Exp 5 | 7 | 1 | -6 | 2.8 | | 1.5 | |
| Exp 6 | 5 | 5 | 0 | 25 | 3.4 | 3.3 | |
| Exp 7 | 7 | 7 | 0 | 24.4 | 7.1 | 4.6 | |
| Exp 8 | 7 | 9 | 2 | 21.2 | 9.5 | 5.3 | |
| Exp 9 | 9 | 7 | -2 | 18.1 | 3.5 | 8.2 | |
| Exp 10 | 9 | 3 | -6 | 18.8 | 2.1 | 4.1 | |
| Exp 11 | 5 | 9 | 4 | 17.8 | 12.3 | 6.9 | |
| Exp 12 | 5 | 7 | 2 | 20.8 | 4.3 | 5.8 | |
| Exp 13 | 3 | 9 | 6 | 16.5 | 5.1 | 7.5 | |
| Exp 14 | 3 | 7 | 4 | 24.2 | 4.2 | 4.2 | |
| Exp 15 | 3 | 5 | 2 | 21.9 | 3.5 | 3.5 | |
| Exp 16 | 3 | 3 | 0 | 24.3 | 2.1 | 2.8 | |
| Exp 17 | 7 | 3 | -4 | 16.9 | 6.7 | 3.6 | |
| Exp 18 | 5 | 3 | -2 | 22.6 | 1.8 | 2.7 | |
| Exp 19 | 1 | 9 | 8 | | 43 | | difficult to control |
| Exp 20 | 1 | 7 | 6 | | 30 | failed | |
| Exp 21 | 1 | 5 | 4 | | | | |

FIG. 22

BIOLOGICAL FLUID SEPARATION DEVICE

CROSS-REFERENCE TO RELATED APPLICATION

The present application claims priority to U.S. Provisional Application Ser. No. 62/347,816 entitled "Biological Fluid Separation Device" filed Jun. 9, 2016, the entire disclosure of which is hereby incorporated by reference.

BACKGROUND OF THE INVENTION

1. Field of the Disclosure

The present disclosure relates generally to devices adapted for use with biological fluids. More particularly, the present disclosure relates to devices adapted for separating components of biological fluids.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Blood samples contain a whole blood portion and a plasma portion. Plasma separation from whole blood has been traditionally achieved by centrifugation which typically takes 15 to 20 minutes and involves heavy labor or complex work flow. Recently there are other technologies that have been used or tried to separate plasma such as sedimentation, fibrous or non-fibrous membrane filtration, lateral flow separation, microfluidics cross flow filtration and other microfluidics hydrodynamic separation techniques. However many of those technologies have various challenges arranging from poor plasma purity, analyte bias or requiring specific coating to prevent analyte bias, high hemolysis, requiring dilution, long separation time, and/or difficult to recover the plasma. For example, most membrane based separation technologies suffer from an analyte bias problem, and often require specific coating treatments for the target analytes.

SUMMARY OF THE INVENTION

The present disclosure provides a blood separation device and a separation process that allows high quality plasma to be generated and a blood separation device that allows a single pressure source such as an evacuated tube to power the whole plasma separation process. The device design is simple, low cost and disposable. The plasma separation process is fast, easy to operate and produces high quality plasma samples from whole blood. It is scalable from sample size of micro liters to milliliters. The separation process does not require any hardware or electric power. It is operated by pressures which can be generated by using a syringe draw and/or an evacuated tube. The quality of the separated plasma is comparable to that of tube plasma generated by centrifugation and suitable for various diagnostic needs.

In one embodiment, the volume of a plasma collection container is selected to provide a trans-membrane pressure of the desired magnitude. A blood separation device of the present disclosure matches the plasma chamber volume, the blood chamber volume, and the applied single pressure source so that the correct trans-membrane pressure and shear rate is obtained.

In accordance with an embodiment of the present invention, a blood separation device adapted to receive a blood sample having a whole blood portion and a plasma portion includes a housing defining a first chamber having a first chamber inlet and a first chamber outlet, a second chamber having a second chamber outlet, and including a separation member disposed between the first chamber and the second chamber, wherein the first chamber is adapted to receive the blood sample; an actuator; and a line in communication with the actuator and a portion of the first chamber, wherein actuation of the actuator draws the blood sample into the first chamber and the separation member is adapted to allow the plasma portion to pass through the separation member to the second chamber.

In one configuration, the separation member is adapted to trap the whole blood portion in the first chamber and allow the plasma portion to pass through the separation member and into the second chamber. In another configuration, the blood separation device includes a plasma collection container in communication with the second chamber outlet. In yet another configuration, a single actuator provides a first pressure to a portion of the first chamber via the line and a second pressure to a portion of the second chamber. In one configuration, the second pressure is regulated by a porosity of the separation member and a volume of the second chamber. In another configuration, the second pressure is regulated by a porosity of the separation member, a volume of a blood collection tube, a volume of the second chamber, and a volume of a plasma collection tube. In another configuration, the actuator is a vacuum source. In yet another configuration, the actuator is an evacuated tube. In one configuration, the separation member comprises a track-etched membrane. In another configuration, the blood separation device includes a vent transitionable between an open position and a closed position.

In accordance with another embodiment of the present invention, a blood separation device adapted to receive a blood sample having a whole blood portion and a plasma portion includes a housing defining a first chamber having a first chamber inlet and a first chamber outlet, a second chamber having a second chamber outlet, and including a separation member disposed between the first chamber and the second chamber, wherein the first chamber is adapted to receive the blood sample; an actuator in communication with a portion of the first chamber; and a plasma collection container in communication with the second chamber outlet, wherein actuation of the actuator draws the blood sample into the first chamber and the separation member is adapted to allow the plasma portion to pass through the separation member to the second chamber.

In one configuration, a single actuator provides a first pressure to a portion of the first chamber and a second pressure to a portion of the second chamber. In another configuration, the second pressure is regulated by a porosity of the separation member and the plasma collection container. In yet another configuration, the blood separation device includes a first resister in communication with the first pressure. In one configuration, the blood separation device includes a second resister in communication with the second pressure. In another configuration, the separation member is adapted to trap the whole blood portion in the first chamber and allow the plasma portion to pass through the separation member and into the second chamber. In yet another configuration, the actuator is a vacuum source. In one configuration, the actuator is a syringe draw. In another configuration, the actuator is an evacuated tube. In yet another configuration, the separation member comprises a track-etched membrane. In one configuration, the blood separation device includes a vent transitionable between an open position and a closed position.

In accordance with another embodiment of the present invention, a blood separation device adapted to receive a blood sample having a whole blood portion and a plasma portion includes a housing defining a first chamber having a first chamber inlet and a first chamber outlet, a second chamber having a second chamber outlet, and including a separation member disposed between the first chamber and the second chamber, wherein the first chamber is adapted to receive the blood sample; a single actuator in communication with a portion of the first chamber; and a plasma collection container in communication with the second chamber outlet, wherein actuation of the single actuator draws the blood sample into the first chamber and the separation member is adapted to allow the plasma portion to pass through the separation member to the second chamber, and wherein the single actuator provides a pressure source that is split between the first chamber and the second chamber, and the blood separation device includes a regulator to regulate a ratio of the split.

In accordance with another embodiment of the present invention, a blood separation device adapted to receive a blood sample having a whole blood portion and a plasma portion includes a housing defining a first chamber having a first chamber inlet and a first chamber outlet, a second chamber having a second chamber outlet, and including a separation member disposed between the first chamber and the second chamber, wherein the first chamber is adapted to receive the blood sample; a single actuator in communication with a portion of the first chamber; and a plasma collection container in communication with the second chamber outlet, wherein actuation of the single actuator draws the blood sample into the first chamber and the separation member is adapted to allow the plasma portion to pass through the separation member to the second chamber, and wherein the single actuator provides a pressure source that is directed only to a side of the first chamber, with a volume of a side of the second chamber configured to control a ratio of pressure between the side of the first chamber and the side of the second chamber.

In accordance with another embodiment of the present invention, a blood separation device adapted to receive a blood sample having a whole blood portion and a plasma portion includes a housing defining a first chamber having a first chamber inlet and a first chamber outlet, a second chamber having a second chamber outlet, and including a separation member disposed between the first chamber and the second chamber, wherein the first chamber is adapted to receive the blood sample; an actuator in communication with a portion of the first chamber; and a plasma collection container in communication with the second chamber outlet, wherein the actuator provides a first pressure to a portion of the first chamber for tangential flow of the blood sample and provides a second pressure to a portion of the second chamber to create a trans-membrane pressure and to drive the plasma portion flow into the plasma collection container.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 5 is a table listing the performance of a prior art method of yielding plasma.

FIG. 6 is a table listing the performance of a method and device of yielding plasma in accordance with an embodiment of the present invention.

FIG. 7 is a table listing the performance of a method and device of yielding plasma in accordance with an embodiment of the present invention.

FIG. 12 is a table listing the performance of a method and device of yielding plasma in accordance with an embodiment of the present invention.

FIG. 18 is a table listing the performance of devices of yielding plasma in accordance with an embodiment of the present invention.

FIG. 22 is a table listing experiment settings and the performance of a device yielding plasma in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1A:
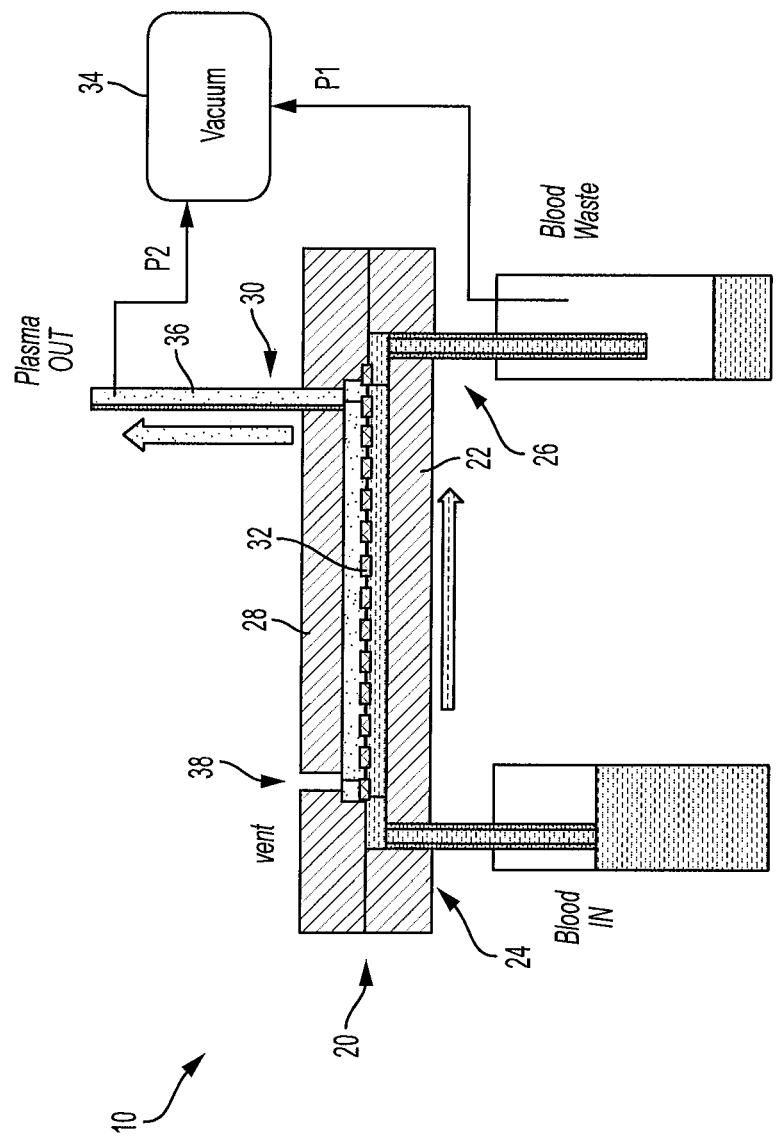
FIG. 1A is a schematic representation of a blood separation device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 2:
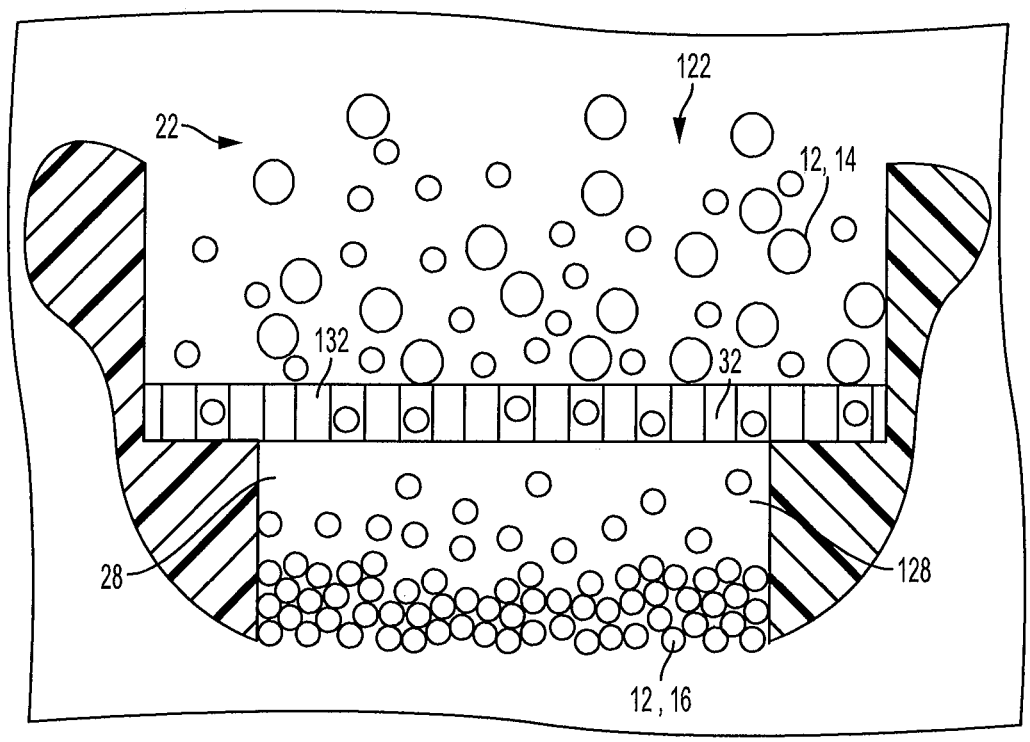
FIG. 2 is a sectional view of a separation member of the blood separation device of FIGS. 1A, 4A, 11A, and 13-17 in accordance with embodiments of the present invention, with the separation member separating a plasma portion of a blood sample from a whole blood portion of the blood sample.

FIG. 1A illustrates an exemplary embodiment of a blood separation device of the present disclosure. Referring to FIGS. 1A and 2, a blood separation device 10 of the present disclosure is adapted to receive a blood sample 12 having a whole blood portion 14 and a plasma portion 16. The present disclosure provides a blood separation device and a separation process that allows high quality plasma to be generated in less than 1 minute and a blood separation device that allows a single pressure source such as an evacuated tube to power the whole plasma separation process. The device design is simple, low cost and disposable. The plasma separation process is fast, easy to operate and produces high quality plasma samples from whole blood. It is scalable from sample size of micron liters to milliliters. The separation process does not require any hardware or electric power. It is operated by pressures which can be generated by using a syringe draw and/or an evacuated tube. The quality of the separated plasma is comparable to that of tube plasma generated by centrifugation and suitable for various diagnostic needs.

In one embodiment, after collecting a blood sample, the blood separation device 10 is able to separate a plasma portion of the blood sample from the whole blood portion as described in more detail below. In one embodiment, after separation, the blood separation device 10 is able to transfer the plasma portion of the blood sample to a point-of-care testing device.

A blood separation device of the present disclosure matches the plasma chamber volume, the blood chamber volume, and the applied single pressure source so that the correct trans-membrane pressure and shear rate is obtained.

Referring to FIGS. 1A and 2, a blood separation device 10 generally includes a housing 20, a first chamber or blood chamber 22, a first chamber inlet 24, a first chamber outlet 26, a second chamber or plasma chamber 28, a second chamber outlet 30, a separation member or membrane 32, an actuator 34, a plasma collection container 36, and a vent 38.

In one embodiment, the housing 20 defines a first chamber 22 and a second chamber 28. The first chamber 22 is adapted to receive a blood sample 12. The first chamber 22 includes a first chamber inlet 24 and a first chamber outlet 26. The second chamber 28 includes a second chamber outlet 30. In one embodiment, the blood separation device 10 includes a separation member 32 that is disposed between the first chamber 22 and the second chamber 28. In one embodiment, the blood separation device 10 includes a single channel or chamber on a blood side as opposed to multiple channels that are used in conventional devices. A configuration of the present disclosure allows for a high flow rate, high shear, and results in a greater yield.

In one embodiment, the blood separation device 10 includes a plasma collection container 36 that is in communication with the second chamber outlet 30. The plasma collection container 36 is able to collect and store the separated plasma 16.

In one embodiment, the plasma collection container 36 includes a non-deformable plasma chamber. In such an embodiment, the volume of the plasma collection container 36 is selected to provide a trans-membrane pressure of the desired magnitude. The volume of the plasma collection container 36 is matched with the blood chamber volume and/or the container volume, and the applied single pressure source so that the correct trans-membrane pressure and shear rate is obtained. In other embodiments, the plasma collection container 36 may be deformable.

In one embodiment, the blood separation device 10 includes a vent 38 that is transitionable between an open position and a closed position.

The separation member 32 is adapted to trap the whole blood portion 14 in the first chamber 22 and allow the plasma portion 16 to pass through the separation member 32 and into the second chamber 28, as shown in FIG. 2.

In one embodiment, the separation member 32 comprises a track-etched membrane. In one embodiment, the track-etched membrane comprises a polycarbonate membrane with a pore size of 0.4 um and a pore density of $1.5 \times 10^8$/cm$^2$. In one embodiment, a separation member 32 includes a pore size from 0.2 to 1 um. In one embodiment, a separation member 32 is formed of a material that can be PC, PET, PP or other materials. In one embodiment, a separation member 32 is hydrophobic. In one embodiment, the pore density of a separation member 32 can be from $5 \times 10^8$/cm$^2$ to $1 \times 10^6$/cm$^2$. In one embodiment, the thickness of a separation member 32 can be from 8 to 100 um. In one embodiment, the water flow rate of a separation member 32 can be in the range of 2.5 to 300 mL/min/cm$^2$ through the separation member 32.

In other embodiments, the separation member 32 may be either hollow fiber membrane filters or flat membrane filters. Membrane filter pore size and porosity can be chosen to optimize separation of clean (i.e., red blood cell free, white blood cell free, and platelet free) plasma 16 in an efficient manner. In other embodiments, the separation member 32 may comprise any filter that is able to trap the whole blood portion 14 in the first chamber 22 and allow the plasma portion 16 to pass through the separation member 32 and into the second chamber 28.

In one embodiment, the blood separation device 10 includes an actuator 34. The actuator 34 is in communication with a portion of the first chamber 22 and a portion of the second chamber 28. In one embodiment, actuation of the actuator 34 draws a blood sample 12 into the first chamber 22 and the separation member 32 is adapted to allow the plasma portion 16 of the blood sample 12 to pass through the separation member 32 to the second chamber 28. In one embodiment, the separation member 32 is adapted to trap the whole blood portion 14 in the first chamber 22 and allow the plasma portion 16 to pass through the separation member 32 and into the second chamber 28.

Referring to FIG. 1A, the blood separation device 10 includes a blood chamber 22, a plasma chamber 28, and a separation member 32 that is operated by a pressure source, e.g., an actuator 34, to drive the blood flow and plasma flow. In one embodiment, the actuator 34 is a vacuum source. In some embodiments, the vacuum source can be from syringes, evacuated tubes or other vacuum generators. In other embodiments, a practical power source can be achieved by using a syringe pulled manually or with a syringe pump to create the vacuum. The power source can also be an evacuated tube, or other vacuum source. In alternative embodiments, the plasma separation can be achieved by pushing blood from the blood inlet side, e.g., the first chamber inlet 24, to flow over the separation member 32. In this case the pressure source is a positive pressure which can be generated by syringes or compressed air or other gaseous medium.

A blood separation device 10 of the present disclosure utilizes the tangential flow filtration of biological samples such as separating plasma from a whole blood that is achieved by flowing a blood sample tangentially at a certain shear rate along a membrane surface with selected membrane porosity and applying a trans-membrane pressure that drives plasma to flow through the membrane pores. The balance of the trans-membrane pressure, shear rate and the membrane pore size is critical to ensure a successful separation process. The trans-membrane pressure has to be large enough to allow the plasma flow through the membrane but not too large to drive the blood cells into the pores of the membrane. If the trans-membrane pressure is too large, blood cells can be forced onto the pores of the membrane and block the plasma flow since most of the blood cells are larger than the pore size. When the trans-membrane pressure is extremely large, the trapped blood cells at the membrane surface can break and cause other issues such as high hemolysis in the plasma. Shear rate of the tangential flow also affects the cell's tendency to stick on membrane pores and surfaces. Higher shear rate reduces the tendency of blood cells sticking to the membrane pores. Lower shear rate increases the opportunity of cells to stick on the membrane pore entrance of the membrane. This shear rate affects the critical trans-membrane pressure where the device can operate. Higher shear rate can make the process tolerate higher trans-membrane pressure without risking the blood cells to be trapped on the pores of the membrane. On the other hand, the shear rate can be too large and break the cells during the tangential flow of the blood sample. This is mainly caused by the shear stress exceeding the cell membrane strength, causing the cell rupture or releasing hemoglobin under large deformation due to the shear stress. This shear stress affects both blood cells in the bulk and those stuck on membrane surface. Pore size of the membrane also affects the cells tendency to get stuck or trapped in the pores of the membrane. Larger pore size tends to allow cells to stick or pass through the membrane under the same trans-membrane pressure and shear rate. A blood separation device 10 of the present disclosure utilizes an essential balance of the shear rate, trans-membrane pressure, and the pore size of the membrane to achieve good tangential flow plasma separation. The essential balance of these parameters using a blood separation device 10 of the present disclosure can lead to high separation efficiency (plasma yield per unit area) and high plasma quality (low PFH).

In one embodiment, the pressure source is the pressure to drive the blood flow and to create the trans-membrane pressure as the blood flows through the chamber. In one embodiment, the trans-membrane pressure should be large enough to drive the plasma flow through the separation member 32 but small enough to keep blood cells from being trapped at the pore entrance or dragged through the membrane pore. In one embodiment, the "net transmembrane pressure" should be less than 5 psi, preferably less than 2.5 psi.

A blood separation device 10 of the present disclosure also utilizes an essential balance of the geometry of the device, e.g., plasma separation chamber height, width and length. For example, the volume of the plasma collection container 36 is selected to provide a trans-membrane pressure of the desired magnitude. The volume of the plasma collection container 36 is matched with the blood chamber volume, and the applied single pressure source so that the correct trans-membrane pressure and shear rate is obtained. The geometry parameters not only affect the shear rate directly, but also the trans-membrane pressure itself. Geometry can significantly affect the uniformity of the trans-membrane pressure along the length of the tangential flow over the porous membrane. There is a pressure drop along the flow path by fluid dynamics. This means that the inlet and outlet pressures in the blood chamber are different and hence trans-membrane pressure could vary along the separation membrane surface of the flow length. This pressure drop or trans-membrane pressure variation has to be small enough so that the maximum trans-membrane pressure (typically at the blood inlet) is within the safety range that prevents high hemolysis. The pressure drop along the flow pass of the membrane surfaces is affected by the flow rate, hydrodynamic geometry (defined by its cross section of the blood chamber), the length of the chamber, the viscosity and density of the blood etc. Smaller hydrodynamic geometry, long flow length and high flow rate will results in large pressure drop and potentially cause large variation in trans-membrane pressure. The balance of the flow rate, chamber cross section and the length of the separation chamber is critical to keep pressure drop minimum and trans-membrane pressure within desired range along the flow (filtration) length.

The geometry of the blood separation device 10 of the present disclosure and the shear rate affect the residence time of the blood in contact with the filtration membrane. This is another important parameter beyond trans-membrane pressure and shear rate. Long residence time allows higher plasma separation efficiency and plasma yield at fixed blood input volume and hematocrit. The residence time can be increased by increasing the chamber length or decreasing the chamber height. They have to be balanced with shear rate and trans-membrane pressure uniformity or pressure drop.

To the inter dependency of the parameters (blood sample, geometry and operating pressures), an overall balance between those parameters is achieved by a blood separation device 10 of the present disclosure to ensure a practical useful plasma separation and that produces high quality, high yield plasma within a desired time frame.

In one embodiment, the pressure to drive the blood flow should be matched to the chamber geometry and targeted flow rate. The flow rate (more relevant to the fluid dynamics is the wall shear rate) should be uniform and large enough to prevent red blood cell deposit on to a membrane surface (cake layer formation). The shear rate should be below a threshold to prevent shear induced hemolysis. This shear induced hemolysis is also dependent on residence time under the shear. The combination effect from shear and time should be controlled.

Figure 1B:
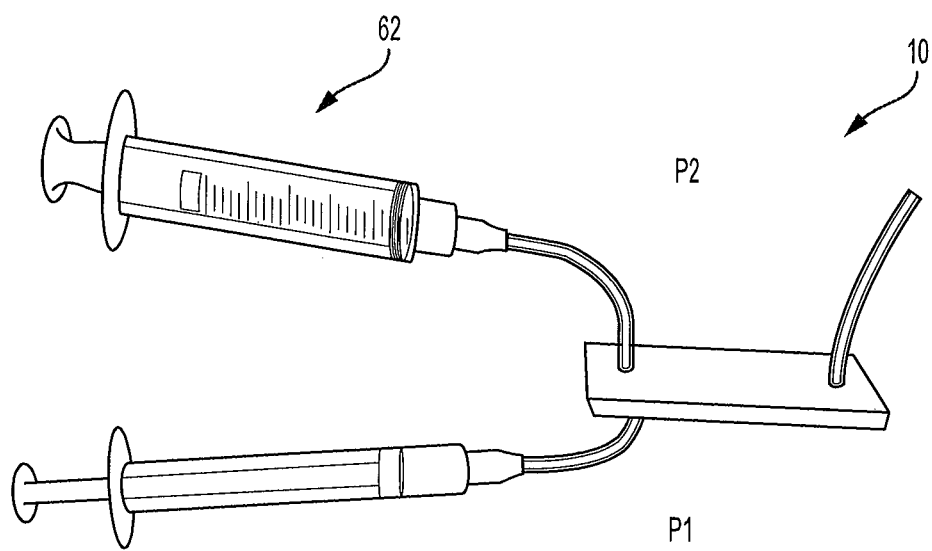
FIG. 1B is a perspective view of a blood separation device in accordance with an embodiment of the present invention.
Figure 1C:
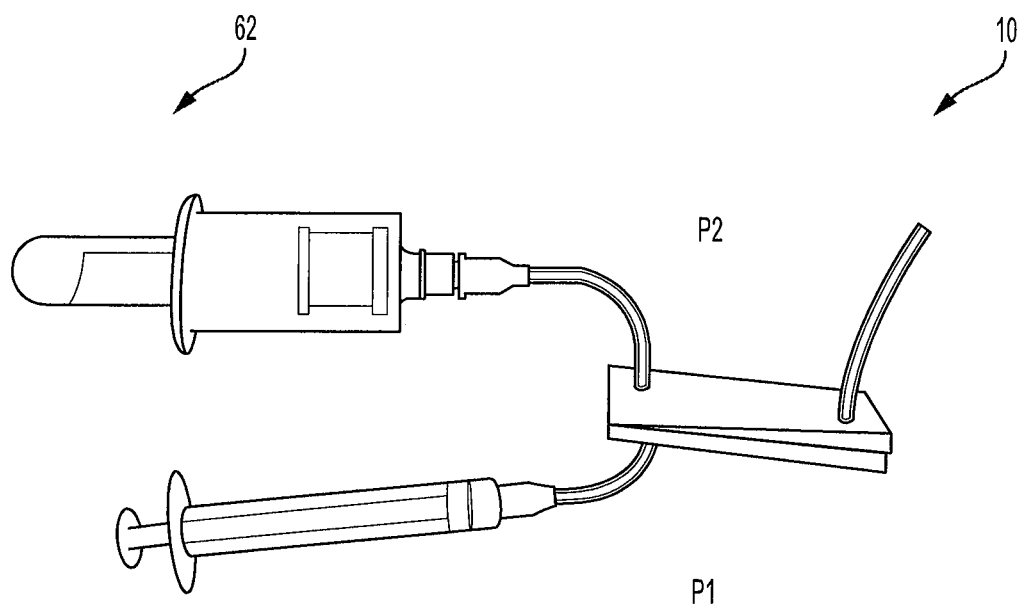
FIG. 1C is a perspective view of a blood separation device in accordance with another embodiment of the present invention.
Figure 1D:
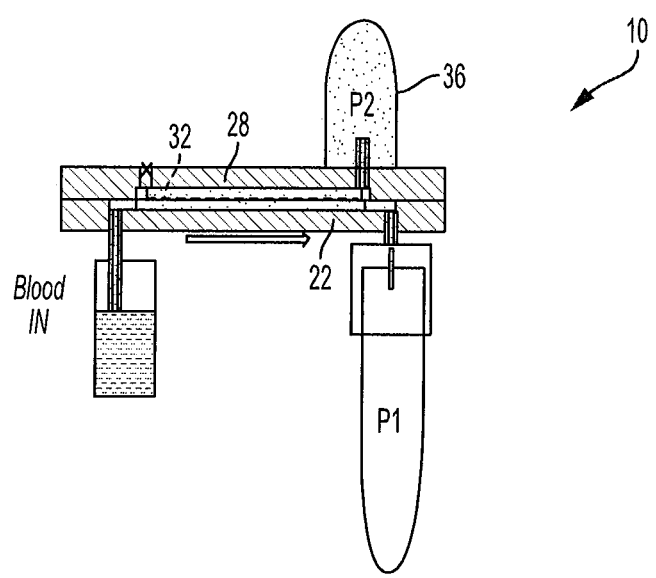
FIG. 1D is a schematic representation of a blood separation device in accordance with another embodiment of the present invention.

Referring to FIG. 1D, in one embodiment, the single power source may be a vacuum containing blood collection tube or an evacuated tube such as a Vacutainer® blood collection tube commercially available from Becton, Dickinson and Company. The vacuum containing blood collection tube provides a first pressure P1 to a portion of the first chamber 22 for tangential flow of the blood and also provides a second pressure P2 to a portion of the second chamber 28 to create the trans-membrane pressure and to drive the plasma flow into the plasma collection tube or plasma collection container 36. In one embodiment, the second pressure P2 is obtained when the vacuum containing blood collection tube is actuated, transferring the vacuum power through the cross talk of the separation membrane prior to the blood moving into the blood chamber.

A blood separation device 10 of the present disclosure, that has a vacuum containing blood collection tube as the single power source, achieves an essential balance between the following parameters. The selection of the vacuum containing blood collection tube volume, the vacuum containing blood collection tube pressure, and the volume of the plasma collection container or tube 36 is important to achieve the desired pressures for plasma separation initially. The ratio of the vacuum containing blood collection tube volume to plasma collection tube volume is selected so that the pressure decay in the vacuum containing blood collection tube and the plasma collection tube is comparable during the whole plasma separation process. The pressure and volume of the vacuum containing blood collection tube is selected according to the input blood volume. This balance of the vacuum containing blood collection tube size, pressure and the plasma collection tube volume allows the device to operate at the desired shear rate and trans-membrane pressure range. In one embodiment, typical shear rate can be in the range of 50 to 20,000 l/s. In one embodiment, the trans-membrane pressure can be in the range of 0.1 to 10 psi.

Referring to FIG. 1D, in one embodiment, the separation member or membrane 32 has a pore size of 0.4 um. In one embodiment, the separation member or membrane 32 is a hydrophobic PCTE membrane. In one embodiment, the first chamber or blood chamber 22 is 50 mm×10 mm×0.08 mm. In one embodiment, the second chamber or plasma chamber 28 is 40 mm×10 mm×0.08 mm and includes ridges to support the separation membrane 32. In one embodiment, the input blood comprises 3 mL whole blood of 55% hematocrit.

Referring to FIG. 18, the table lists the results for different combinations of the Vacutainer pressure (12.5 psi and 8 psi) and the plasma collection tube volume (1 mL and 4 mL). The single power source design allows plasma separation that starts at similar initial pressure settings (P1=P2). Low pressure and large plasma collection tube volume induce less hemolysis and tend to increase the plasma separation time. While a 4 mL plasma collection tube generated a higher plasma yield.

Figure 19:
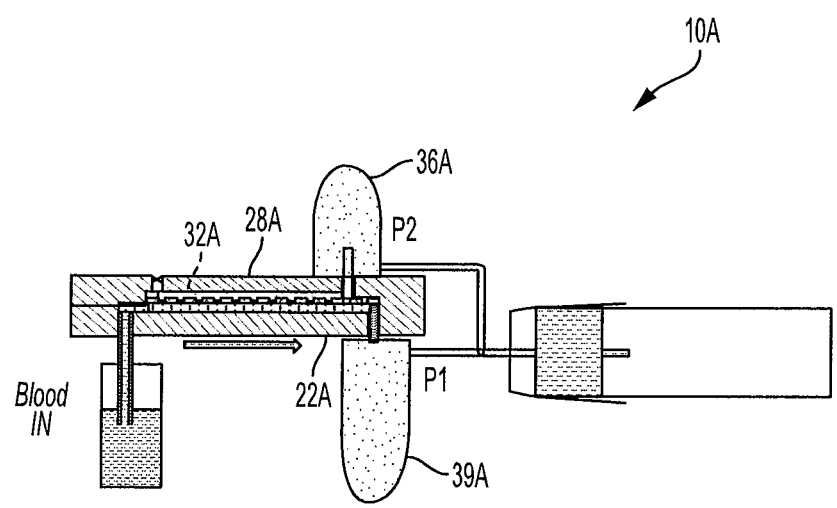
FIG. 19 is a schematic representation of a blood separation device in accordance with another embodiment of the present invention.
Figure 20:
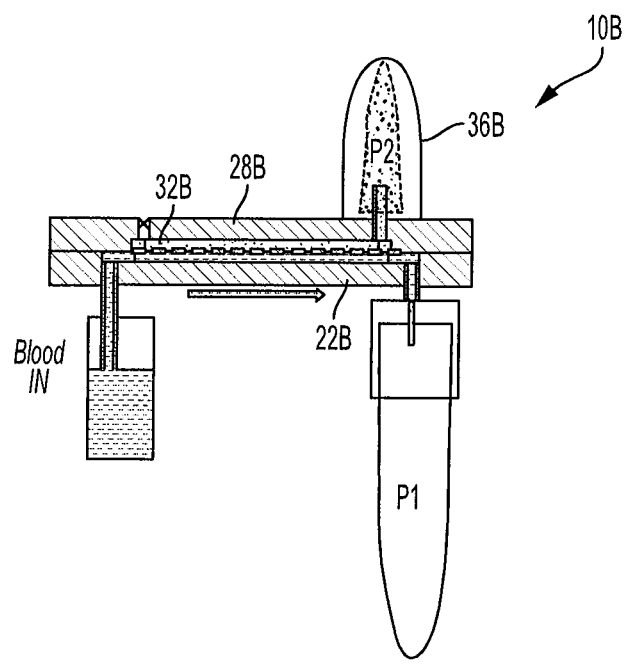
FIG. 20 is a schematic representation of a blood separation device in accordance with another embodiment of the present invention.

FIGS. 19-20 illustrate other exemplary embodiments of a blood separation device of the present disclosure. Referring to FIGS. 2 and 19, a blood separation device 10A of the present disclosure is adapted to receive a blood sample 12 having a whole blood portion 14 and a plasma portion 16. The present disclosure provides a blood separation device and a separation process that allows high quality plasma to be generated and a blood separation device that allows a single pressure source such as an evacuated tube to power the whole plasma separation process. The device design is simple, low cost and disposable. The plasma separation process is fast, easy to operate and produces high quality plasma samples from whole blood. It is scalable from sample size of micron liters to milliliters. The separation process does not require any hardware or electric power. It is operated by pressures which can be generated by using a syringe draw and/or an evacuated tube. The quality of the separated plasma is comparable to that of tube plasma generated by centrifugation and suitable for various diagnostic needs.

In one embodiment, after collecting a blood sample, the blood separation device 10A is able to separate a plasma portion of the blood sample from the whole blood portion. In one embodiment, after separation, the blood separation device 10A is able to transfer the plasma portion of the blood sample to a point-of-care testing device.

Referring to FIG. 19, in one embodiment, a blood separation device 10A having a single power source design includes a blood chamber 22A and a plasma chamber 28A, connected through a separation membrane 32A. The blood separation device 10A includes a plasma collection tube 36A, a waste blood collection tube 39A attached to the plasma outlet and waste blood outlet respectively, and a single actuator. In one embodiment, the actuator can be an evacuated tube, a syringe draw, a constant vacuum pressure supply or any other vacuum power source. The advantage of this configuration is that it can be operated using a constant vacuum power source and keeps the pressure P1 and P2 essentially the same during the whole plasma separation process. There is no need to balance the volume ratio of the plasma collection tube and the waste blood collection tube. However, when an evacuated tube is used as the power, the total volume of both collection tubes need to be compatible with the evacuated tube power source.

Referring to FIG. 20, in one embodiment, a blood separation device 10B having a single power source design includes a blood chamber 22B and a plasma chamber 28B, connected through a separation membrane 32B. The blood separation device 10B includes a flexible plasma collection tube 36B and a blood separation actuator. There are other configurations that offer flexible or adjustable volume for the plasma collection tubes. The actuator can be an evacuated tube, a syringe draw, a constant vacuum pressure supply or any other vacuum power source. The flexible plasma collection tube regulates the pressures to a more uniform decay and prevents potential high trans-membrane pressure. It can also act as a plasma dispenser after the plasma separation is completed.

A blood separation device of the present disclosure may include other exemplary embodiments. For example, in one embodiment, the blood chamber 22 includes a long blood chamber length and lower blood chamber height to improve the plasma separation efficiency. This may also increase a flow resistance of the blood, and thus require a higher pressure to drive the blood flow through the chamber. In one embodiment, a wider blood chamber can reduce flow resistance and the pressure needed to drive the blood flow. In some embodiments, the blood chamber geometry is balanced and/or configured for the targeted plasma yield and corresponding power source to operate the device.

Referring to FIGS. 1B and 1C, in one embodiment, the actuator 34 includes a first actuator 60 which provides a first pressure P1 to a portion of the first chamber 22 and a second actuator 62 which provides a second pressure P2 to a portion of the second chamber 28. Referring to FIG. 1B, in one embodiment, the first actuator 60 and the second actuator 62 may be syringes. In such an embodiment, a first syringe draws from the first chamber outlet 26 and a second syringe draws from the second chamber outlet 30. Referring to FIG. 1C, in one embodiment, the first actuator 60 may be a syringe and the second actuator 62 may be an evacuated tube. In such an embodiment, an evacuated tube draws from the first chamber outlet 26 and a syringe draws from the second chamber outlet 30. In such an embodiment, an evacuated tube draws from the first chamber outlet and a secondary evacuated tube draws from the second chamber outlet.

In one embodiment, the blood flow and plasma separation using a blood separation device 10 of the present disclosure is powered by pressure at the inlet, e.g., the first chamber inlet 24, and the outlet, e.g., the first chamber outlet 26 and/or the second chamber outlet 30. In one embodiment, the pressure at the blood inlet, e.g., the first chamber inlet 24, may be set to zero, the pressure at the first chamber outlet 26 may be set at −5 psi, and the pressure at the plasma outlet, e.g., the second chamber outlet 26, may be set at −3 psi.

In another embodiment, the pressure at the blood inlet, e.g., the first chamber inlet 24, may be set to zero, the pressure at the first chamber outlet 26 may be set at −7 psi, and the pressure at the plasma outlet, e.g., the second chamber outlet 26, may be set at −5 psi. In another embodiment, the pressure at the blood inlet, e.g., the first chamber inlet 24, may be set to zero, the pressure at the first chamber outlet 26 may be set at −7 psi, and the pressure at the plasma outlet, e.g., the second chamber outlet 26, may be set at −7 psi. In one embodiment, the pressure source is a vacuum source.

In one embodiment, the vent 38 is blocked during the plasma separation process and is optionally opened at the end of the plasma separation process to recover all of the plasma 16 from the plasma chamber 28. The pressure setting can be adjusted to specific flow (or shear) rate. In order to achieve short separation time, a higher flow rate and shear rate are desired. In one embodiment, a blood flow rate of 3 to 5 mL/min can be achieved using a blood separation device 10 of the present disclosure.

A blood separation device 10 of the present disclosure provides a balanced blood chamber with a large chamber length, a small chamber height and a large chamber width that has a great separation efficiency. The pressure settings allow for a high flow rate and shear rate within a design target of separation time and input blood volume. Pressure settings also allow proper transmembrane pressure during the separation process. The shear rate prevents blood cake formation as blood flows through the chamber over the membrane surface.

Referring to FIG. 1A, use of a blood separation device 10 of the present disclosure will now be described. In one embodiment, as described above, the blood separation device 10 includes a blood chamber 22 and a plasma chamber 28 which are separated by a separation member or membrane 32, e.g., a track etched membrane. In one embodiment, the membrane 32 is part of the blood chamber 22 and at the same time part of the plasma chamber 28. The blood chamber 22 has a blood inlet, e.g., a first chamber inlet 24, and an outlet, e.g., a first chamber outlet 26. The plasma chamber 28 has one or multiple outlets, e.g., a second chamber outlet 30. Blood flows in through the inlet 24 of the blood chamber 22 and tangentially over the membrane 32 surface, and exits from the outlet 26 of the blood chamber 22. Plasma 16 flows through the membrane 32 and enters the plasma chamber 28 which can be collected or stored in a secondary plasma container, e.g., a plasma collection container 36, for further diagnostic tests. For example, in one embodiment, after separation, the blood separation device 10 is able to transfer the plasma portion of the blood sample to a point-of-care testing device.

Figure 3:
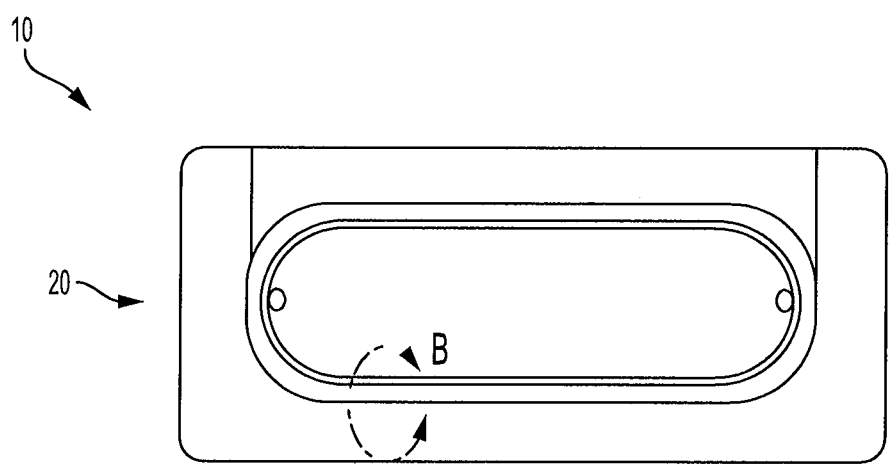
FIG. 3 is a top view of a portion of a chamber of a blood separation device in accordance with an embodiment of the present invention.

In one embodiment, the blood chamber 22 can be designed to allow tangential flow of the blood over the membrane 32 surface which can have different shapes such as but not limited to rectangular, spiral or serpentine etc. The size of the chamber can be varied to meet the application needs for the plasma volume. The inlet 24 and outlet 26 of the blood chamber 22 may be at a non-filtration area to maximize the tangential flow. In one embodiment, the plasma chamber 28 may match the blood chamber 22 to allow efficient utilization of the membrane 32. In one embodiment, referring to FIG. 3, a design example may include a rectangular chamber. In one exemplary embodiment, the blood chamber 22 is 10 mm wide and 50 mm long with the inlet 24 and the outlet 26 at each end of the blood chamber 22. In one embodiment, the blood chamber height is 0.08 mm. In one embodiment, the plasma chamber is 10 mm wide and 40 mm long with outlets at each end. In one embodiment, the plasma chamber height can be from 0.02 mm to 2 mm. In one embodiment, the blood chamber height is 0.08 mm. In one embodiment, ridges are created inside the plasma chamber 28 to support the membrane 32. The membrane 32 can be optionally secured onto the ridges to prevent sagging. Alternatively the ridges can be built in the blood chamber 22 or on both chambers. In one embodiment, the track-etched membrane is a polycarbonate membrane with a pore size of 0.4 um and pore density of $1.5 \times 10^8/cm^2$.

Figure 4A:
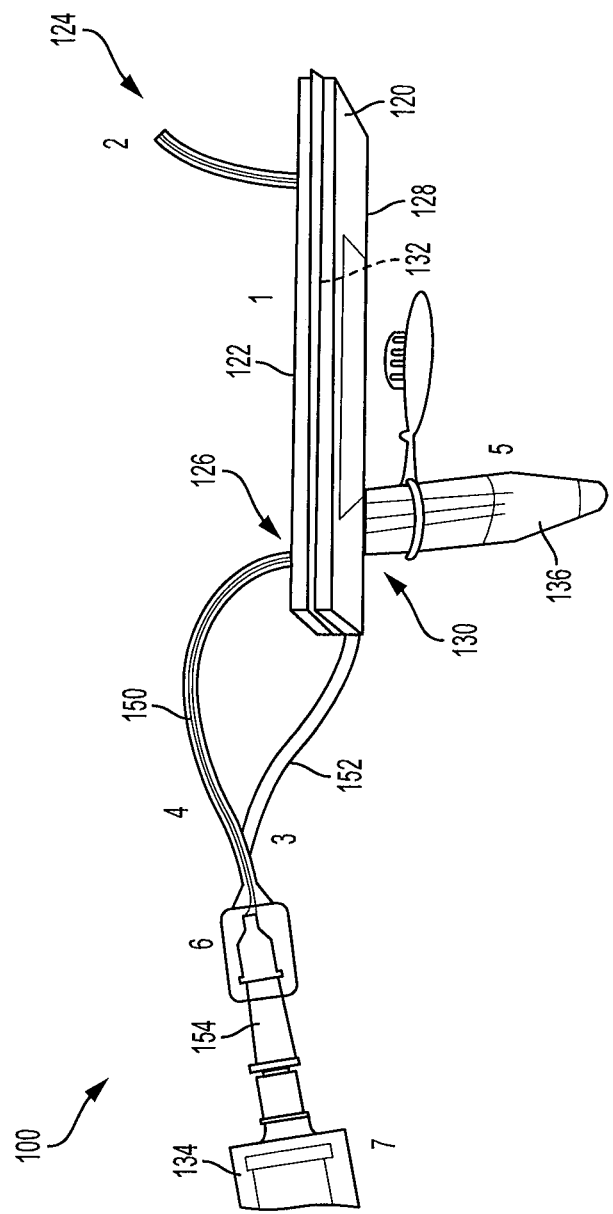
FIG. 4A is a perspective view of a blood separation device in accordance with another embodiment of the present invention.
Figure 4B:
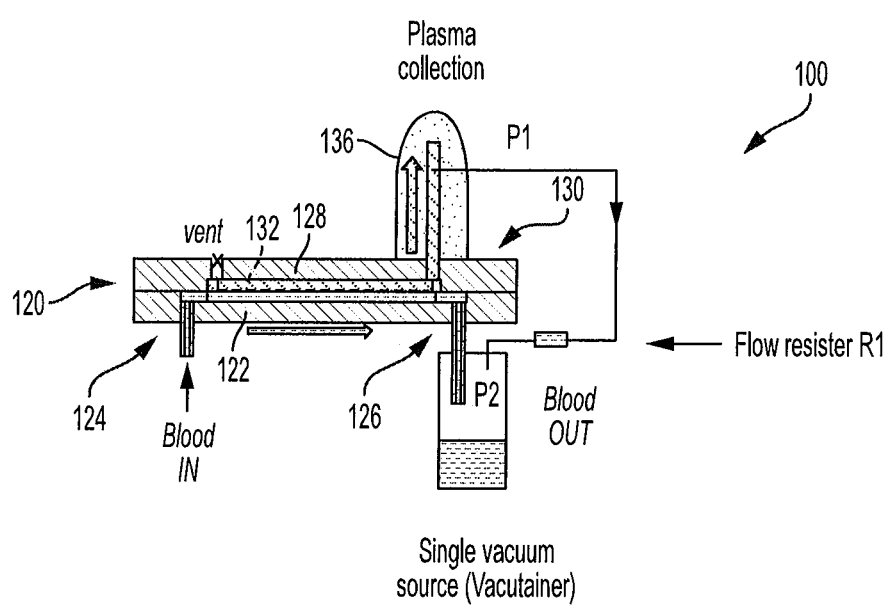
FIG. 4B is a schematic representation of a blood separation device in accordance with another embodiment of the present invention.

FIGS. 4A and 4B illustrate another exemplary embodiment of a blood separation device of the present disclosure. Referring to FIGS. 2 and 4A-4B, a blood separation device 100 of the present disclosure is adapted to receive a blood sample 12 having a whole blood portion 14 and a plasma portion 16. The present disclosure provides a blood separation device and a separation process that allows high quality plasma to be generated in less than 1 minute and a blood separation device that allows a single pressure source such as an evacuated tube to power the whole plasma separation process. The device design is simple, low cost and disposable. The plasma separation process is fast, easy to operate and produces high quality plasma samples from whole blood. It is scalable from sample size of micron liters to milliliters. The separation process does not require any hardware or electric power. It is operated by pressures which can be generated by using a syringe draw and/or an evacuated tube. The quality of the separated plasma is comparable to that of tube plasma generated by centrifugation and suitable for various diagnostic needs.

In one embodiment, after collecting a blood sample, the blood separation device 100 is able to separate a plasma portion of the blood sample from the whole blood portion as described in more detail below. In one embodiment, after separation, the blood separation device 100 is able to transfer the plasma portion of the blood sample to a point-of-care testing device.

Referring to FIGS. 4A-4B, a blood separation device 100 generally includes a housing 120, a first chamber or blood chamber 122, a first chamber inlet 124, a first chamber outlet 126, a second chamber or plasma chamber 128, a second chamber outlet 130, a separation member or membrane 132, an actuator 134, a plasma collection container 136, a first line or blood line 150, a second line or plasma line 152, and a merged line 154. In one embodiment, the first line 150 and the second line 152 are merged into line 154.

In one embodiment, the housing 120 defines a first chamber 122 and a second chamber 128. The first chamber 122 is adapted to receive a blood sample 12. The first chamber 122 includes a first chamber inlet 124 and a first chamber outlet 126. The second chamber 128 includes a second chamber outlet 130. In one embodiment, the blood separation device 100 includes a separation member 132 that is disposed between the first chamber 122 and the second chamber 128.

The separation member 132 is adapted to trap the whole blood portion 14 in the first chamber 122 and allow the plasma portion 16 to pass through the separation member 132 and into the second chamber 128, as shown in FIG. 2.

In one embodiment, the separation member 132 comprises a track-etched membrane. In one embodiment, the track-etched membrane comprises a polycarbonate membrane with a pore size of 0.4 um and a pore density of $1.5 \times 10^8/cm^2$. In one embodiment, a separation member 132 includes a pore size from 0.2 to 1 um. In one embodiment, a separation member 132 is formed of a material that can be PC, PET, PP or other materials. In one embodiment, a separation member 132 is hydrophobic. In one embodiment, the pore density of a separation member 132 can be from $5 \times 10^8/cm^2$ to $1 \times 10^6/cm^2$. In one embodiment, the thickness of a separation member 132 can be from 8 to 100 um. In one embodiment, the water flow rate of a separation member 132 can be in the range of 2.5 to 300 mL/min/cm$^2$ through the separation member 132.

In other embodiments, the separation member 132 may be either hollow fiber membrane filters or flat membrane filters. Membrane filter pore size and porosity can be chosen to optimize separation of clean (i.e., red blood cell free, white blood cell free, and platelet free) plasma 16 in an efficient manner. In other embodiments, the separation member 132 may comprise any filter that is able to trap the whole blood portion 14 in the first chamber 122 and allow the plasma portion 16 to pass through the separation member 132 and into the second chamber 128.

In one embodiment, a first line 150 is in communication with the actuator 134 and the first chamber outlet 126. In one embodiment, a second line 152 is in communication with the actuator 134 and the second chamber outlet 130.

In one embodiment, the blood separation device 100 includes a plasma collection container 136 that is in communication with the second chamber outlet 130. The plasma collection container 136 is able to collect and store the separated plasma 16.

In one embodiment, the blood separation device 100 includes a porous material within the second line 152.

In one embodiment, the blood separation device 100 includes an actuator 134. The actuator 134 is in communication with a portion of the first chamber 122 via the first line 150 and a portion of the second chamber 128 via the second line 152. In one embodiment, actuation of the actuator 134 draws a blood sample 12 into the first chamber 122 and the separation member 132 is adapted to allow the plasma portion 16 of the blood sample 12 to pass through the separation member 132 to the second chamber 128. In one embodiment, the separation member 132 is adapted to trap the whole blood portion 14 in the first chamber 122 and allow the plasma portion 16 to pass through the separation member 132 and into the second chamber 128.

In one embodiment, the blood separation device 100 includes a blood chamber 122, a plasma chamber 128, and a separation member 132 that is operated by a pressure source, e.g., an actuator 134, to drive the blood flow and plasma flow. In one embodiment, the actuator 134 is a vacuum source.

In one embodiment, a single actuator provides a first pressure to a portion of the first chamber 122 via the first line 150 and a second pressure to a portion of the second chamber 128 via the second line 152.

The blood separation device 100 with lines 150, 152 provides a system that requires only one pressure source to drive both blood and plasma sides of the device. In one embodiment, the blood separation device 100 provides a system that requires a single pressure source to power the blood separation device 100 and the pressure from the single pressure source can be split between the blood chamber 122 and the plasma chamber 128. In such an embodiment, the blood separation device 100 includes a regulator to regulate the ratio of the split.

In one embodiment, the blood separation device 100 merges two lines 150, 152 into one merged line 154. In one embodiment, a porous material is added to the plasma vacuum line 152 to create air flow resistance. When a vacuum source is connected to the merged vacuum line 154, a majority of the power source is directed to the blood chamber 122 through line 150 and powers the blood flow. A small portion of the vacuum is directed to the plasma chamber 128 through line 152 to drive the plasma flow and trans-membrane pressure. The resister is a porous polymeric disc with 1 micron meter pore size from Porax. The porous material can be in many forms such as fiber, sintered polymeric materials, porous metals or any other air permeable materials. Alternatively, it can also be a small tube or channel built on a device that resists air flow. The merger for the two vacuum lines and porous material can also be built or incorporated on the device directly.

An alternative design of the blood separation device 100 may incorporate a blood reservoir similar to the plasma reservoir for collecting blood waste, instead of using an evacuated tube as the reservoir for the waste blood. This may be beneficial when a centralized vacuum source is used.

Advantageously, the blood separation device 100 of the present disclosure allows a single pressure source to power the whole plasma separation process.

In one embodiment, the device design parameters (balanced blood chamber height, width and length) match the process parameter settings (pressure 1 for driving blood flow and pressure 2 that works with pressure 1 to provide trans-membrane pressure). The matched system provides targeted flow rate and shear rate so that the cake formation is prevented on a membrane surface. The trans-membrane pressure drives plasma flow through the membrane. If the design and process parameters are not matched, the plasma yield will be low and/or hemolysis will occur. This matching is dominated by the design parameters if a certain flow rate and the uniformity of trans-membrane pressure along the length of the membrane are to be achieved. The trans-membrane pressure uniformity is affected by the pressure drop along the chamber length in the blood chamber.

In one embodiment, the flow resister design and its incorporation in the device allow one single pressure source to drive blood flow and form the trans-membrane pressure. The resister allows a small portion of the common vacuum source to be directed to the plasma side and provide continuous sufficient pressure to drive the plasma flow. The flow resister is built in such a manner that it allows the restriction of airflow in the plasma side but does not get into the plasma path. This simplifies the power source requirement and plasma separation process. For example, the plasma separation can be achieved by connecting the device to a blood source and pushing an evacuated tube to the device. Plasma is separated in less than one minute.

Referring to FIG. 5, the performance of a prior art Zahn multichannel design is shown. Such a design was confirmed to produce 50 µL plasma in 10 minutes. This plasma separation method is slow and produces a low yield of plasma.

A blood separation device of the present disclosure provides a significantly improved performance. The device and method of the present disclosure produces about 400 µL plasma in less than 1 minute using one third of the membrane size of the Zahn design. In one embodiment, the blood separation device of the present disclosure uses a blood chamber size of 10 mm×50 mm×0.08 mm and a plasma chamber size of 10 mm×40 mm×0.2 mm with an effective separation membrane area of 10 mm×40 mm. The power source is a 4 mL Vacutainer tube. The input blood is 3 mL at 38% hematocrit. The process generated about 400 µL high quality plasma in one minute with very low hemolysis as indicated by low hemoglobin level in the plasma samples, as shown in FIG. 6. FIG. 6 illustrates plasma separation performance using a blood separation device of the present disclosure with normal heparinized whole blood at 38% hematocrit.

Plasma samples separated by using the method and blood separation device of the present disclosure are also analyzed using Sysmex to determine the residue cells. The purity of the plasma is comparable to the control sample obtained by conventional centrifugation process, as shown in FIG. 7. Blood samples from different donors have been tested and all performed consistently on a blood separation device of the present disclosure. FIG. 7 illustrates plasma purity determined by Sysmex for samples separated using a blood separation device of the present disclosure with normal heparinized whole blood at 46% hematocrit. The method and blood separation device of the present disclosure also performs very well with whole blood at higher hematocrit (55%). The yield is about 250 µL with the input volume of 3 mL as shown in FIG. 7.

Figures 8, 9:
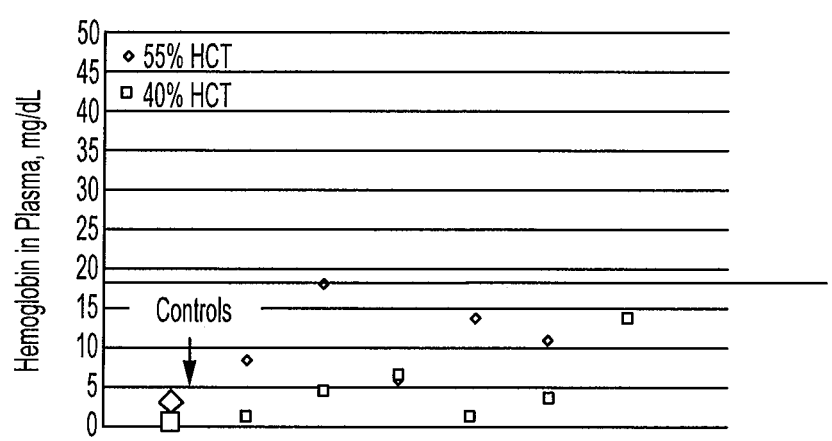
FIG. 8 is a table listing the performance of a method and device of yielding plasma in accordance with an embodiment of the present invention.
FIG. 9 is a graph illustrating the performance of a method and device of yielding plasma in accordance with an embodiment of the present invention.

FIG. 8 illustrates plasma separation performance using a blood separation device of the present disclosure with the heparinized whole blood at 55% hematocrit.

FIG. 9 illustrates Hemoglobin concentration that is determined for plasma samples separated using a blood separation device of the present disclosure with heparinized whole blood at 55% hematocrit. The plasma samples also have very low hemolysis for high hematocrit input blood sample as show in FIG. 9.

Plasma separation is also conducted successfully using the method and blood separation device of the present disclosure with normal fresh blood with no anticoagulant added prior to plasma separation. This allows the device of the present disclosure to work with blood samples directly from line draw without the need to add anticoagulant to the blood. When the device is loaded with heparin in the chambers at target dosage, it can stabilize the blood and plasma during the separation process. High quality plasma is generated and both waste blood and plasma picked up the anticoagulant applied on device. The heparin concentration can be designed to match the tube blood specification of 5 to 28 IU/mL. The plasma samples produced are stable and suitable for further diagnostic purpose. The data from FIG. 10 is obtained using a heparin activity test.

Figure 10:
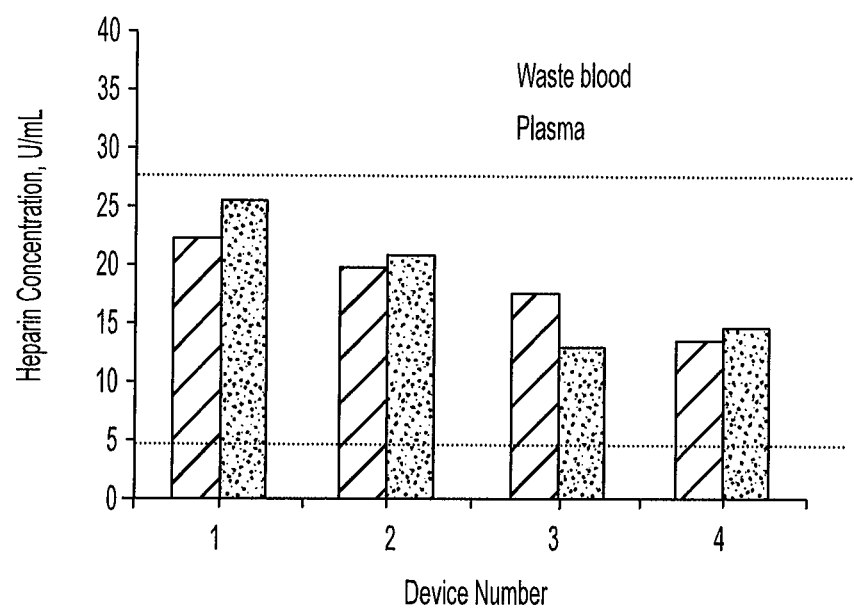
FIG. 10 is a graph illustrating the performance of a method and device of yielding plasma in accordance with an embodiment of the present invention.

FIG. 10 illustrates plasma separation conducted successfully using the method and blood separation device of the present disclosure with normal fresh blood (no anticoagulant added prior to plasma separation) at 42.6% hematocrit. The anticoagulant (heparin) is applied on device chambers and mixed into blood and plasma during plasma separation process.

A blood separation device of the present disclosure could be used for other sample management purposes such as cell isolation, purification and sample concentration.

Figure 11A:
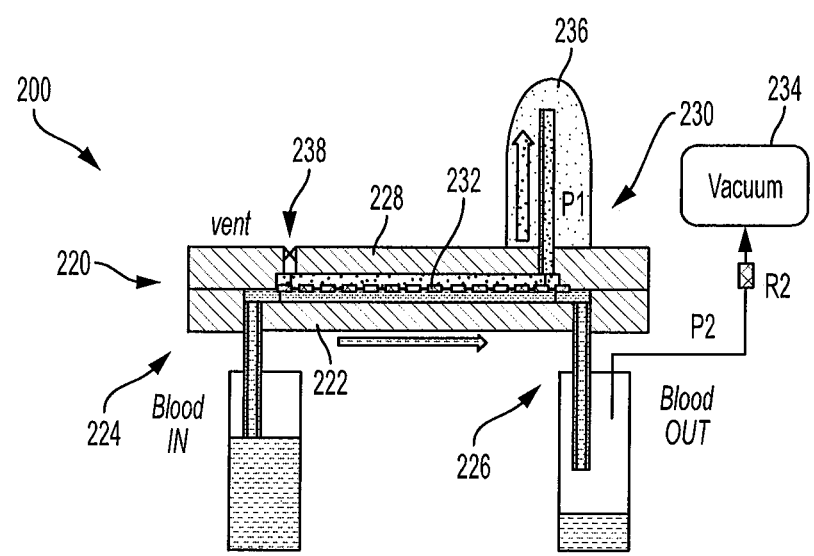
FIG. 11A is a schematic representation of a blood separation device in accordance with another embodiment of the present invention.
Figure 11B:
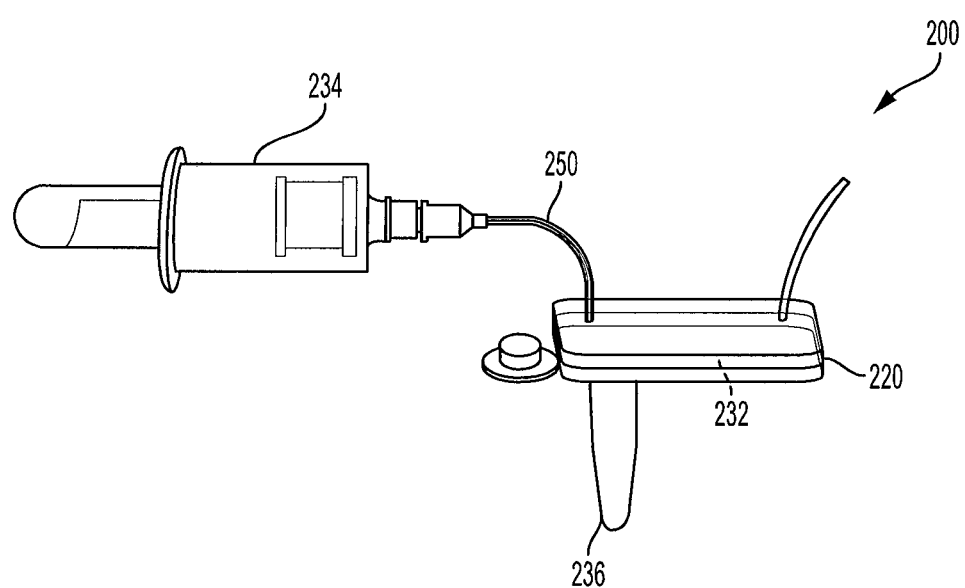
FIG. 11B is a perspective view of a blood separation device in accordance with another embodiment of the present invention.

FIGS. 11A and 11B illustrate another exemplary embodiment of a blood separation device of the present disclosure. Referring to FIGS. 2 and 11A-11B, a blood separation device 200 of the present disclosure is adapted to receive a blood sample 12 having a whole blood portion 14 and a plasma portion 16. The present disclosure provides a blood separation device and a separation process that allows high quality plasma to be generated and a blood separation device that allows a single pressure source such as an evacuated tube to power the whole plasma separation process. The device design is simple, low cost and disposable. The plasma separation process is fast, easy to operate and produces high quality plasma samples from whole blood. It is scalable from sample size of micron liters to milliliters. The separation process does not require any hardware or electric power. It is operated by pressures which can be generated by using a syringe draw and/or an evacuated tube. The quality of the separated plasma is comparable to that of tube plasma generated by centrifugation and suitable for various diagnostic needs.

In one embodiment, after collecting a blood sample, the blood separation device 200 is able to separate a plasma portion of the blood sample from the whole blood portion. In one embodiment, after separation, the blood separation device 200 is able to transfer the plasma portion of the blood sample to a point-of-care testing device.

In one embodiment, the blood separation device 200 allows a vacuum source, such as an evacuated tube, to power the plasma separation process. In one embodiment, the evacuated tube not only drives the blood flow tangentially along a separation member membrane surface, but also provides the trans-membrane pressure needed to allow plasma flow through the membrane. In one embodiment, the blood separation device 200 eliminates the need for a plasma vacuum line and flow resister to regulate the pressure for the plasma side. This is possible because the vacuum power from the evacuated tube can be transferred to the plasma side through the porous TEM instead. The percent of the vacuum power transferred to the plasma side is controlled by the total chamber volume of the plasma side including plasma chamber, plasma storage and connecting channels or tubings.

In one embodiment, a preliminary test was conducted by fixing the evacuated tube to 4 mL to draw from the blood outlet. The total chamber volume in the plasma side was varied from 0.25 to 1 mL. The plasma separation test is stopped when the vacuum is consumed from the 4 mL evacuated tube. FIG. 12 lists the plasma yield at different plasma chamber volumes. Referring to FIG. 12, the plasma yield reached about 350 μL at 1 mL plasma chamber space for 3 mL blood input.

In one embodiment, a preliminary test was conducted by fixing an evacuated tube, such as a Vacutainer tube, to 10 mL to draw from the blood outlet. The total chamber volume in the plasma side was set to 4 mL. The plasma separation test is stopped when the 3 mL whole blood passed through the device. The plasma yield reached about 250 μL with 3 mL input of whole blood at 55% hematocrit.

In one embodiment, the blood separation device 200 utilizes the high air permeability of a track-etched membrane (TEM) to transfer the vacuum power (e.g. an evacuated tube) from blood chamber side to plasma chamber side. This vacuum power is isolated automatically and stored when blood fills in the blood chamber. The stored vacuum power creates enough trans-membrane pressure to allow the plasma separation during the blood flow tangentially along the TEM surface.

Referring to FIGS. 11A and 11B, a blood separation device 200 generally includes a housing 220, a first chamber or blood chamber 222, a first chamber inlet 224, a first chamber outlet 226, a second chamber or plasma chamber 228, a second chamber outlet 230, a separation member or membrane 232, an actuator 234, a plasma collection container 236, and a line or blood line 250.

In one embodiment, the housing 220 defines a first chamber 222 and a second chamber 228. The first chamber 222 is adapted to receive a blood sample 12. The first chamber 222 includes a first chamber inlet 224 and a first chamber outlet 226. The first chamber inlet 224 has a geometry that defines its flow resistance or pressure drop when blood flows through it. That balances the flow resistance of the device and regulate the trans-membrane pressure within a desired range. The geometry of the first chamber inlet 224 can be in different formats to provide the flow resistance. It can be a built in channel, a tubing, a needle, other forms of a fluid flow regulator, or a combination of them.

The second chamber 228 includes a second chamber outlet 230. In one embodiment, the blood separation device 200 includes a separation member 232 that is disposed between the first chamber 222 and the second chamber 228.

The separation member 232 is adapted to trap the whole blood portion 14 in the first chamber 222 and allow the plasma portion 16 to pass through the separation member 232 and into the second chamber 228, as shown in FIG. 2.

In one embodiment, the separation member 232 comprises a track-etched membrane. In one embodiment, the track-etched membrane comprises a polycarbonate membrane with a pore size of 0.4 um and a pore density of $1.5 \times 10^8/cm^2$. In one embodiment, a separation member 232 includes a pore size from 0.2 to 1 um. In one embodiment, a separation member 232 is formed of a material that can be PC, PET, PP or other materials. In one embodiment, a separation member 232 is hydrophobic. In one embodiment, the pore density of a separation member 232 can be from $5 \times 10^8/cm^2$ to $1 \times 10^6/cm^2$. In one embodiment, the thickness of a separation member 232 can be from 8 to 100 um. In one embodiment, the water flow rate of a separation member 232 can be in the range of 2.5 to 300 mL/min/cm$^2$ through the separation member 232.

In other embodiments, the separation member 232 may be either hollow fiber membrane filters or flat membrane filters. Membrane filter pore size and porosity can be chosen to optimize separation of clean (i.e., red blood cell free, white blood cell free, and platelet free) plasma 16 in an efficient manner. In other embodiments, the separation member 232 may comprise any filter that is able to trap the whole blood portion 14 in the first chamber 222 and allow the plasma portion 16 to pass through the separation member 232 and into the second chamber 228.

In one embodiment, a line 250 is in communication with the actuator 234 and a portion of the first chamber 222. In one embodiment, the blood separation device 200 includes a plasma collection container 236 that is in communication with the second chamber outlet 230. The plasma collection container 236 is able to collect and store the separated plasma 16.

In one embodiment, the blood separation device 200 includes an actuator 234. In one embodiment, actuation of the actuator 234 draws a blood sample 12 into the first chamber 222 and the separation member 232 is adapted to allow the plasma portion 16 of the blood sample 12 to pass through the separation member 232 to the second chamber 228. In one embodiment, the separation member 232 is adapted to trap the whole blood portion 14 in the first chamber 222 and allow the plasma portion 16 to pass through the separation member 232 and into the second chamber 228.

In one embodiment, the blood separation device 200 includes a blood chamber 222, a plasma chamber 228, and a separation member 232 that is operated by a pressure source, e.g., an actuator 234, to drive the blood flow and plasma flow. In one embodiment, the actuator 234 is a vacuum source. In one embodiment, the actuator 234 is an evacuated tube. In one embodiment, the actuator 234 is a syringe.

The blood separation device 200 provides a system that requires only one pressure source to drive both blood and plasma sides of the device. In one embodiment, a single actuator provides a first pressure to a portion of the first chamber 122 via the line 250 and a second pressure to a portion of the second chamber 228. In one embodiment, the second pressure is regulated by a porosity of the separation member 232 and a volume of the second chamber 228. Advantageously, the blood separation device 200 of the present disclosure allows a single pressure source to power the whole plasma separation process.

The blood separation device 200 provides a system that requires only one pressure source to drive both blood and plasma sides of the device. In one embodiment, the blood separation device 200 provides a system that requires a single pressure source to power the blood separation device 200 and that pressure source is directed only to the side of the blood chamber 222, with the volume of the side of the plasma chamber 228 and plasma container chosen so as to control the ratio of pressure between the blood and plasma sides of the blood separation device 200.

In one embodiment, the blood separation device 200 includes a vent 238 that is transitionable between an open position and a closed position.

Figure 13:
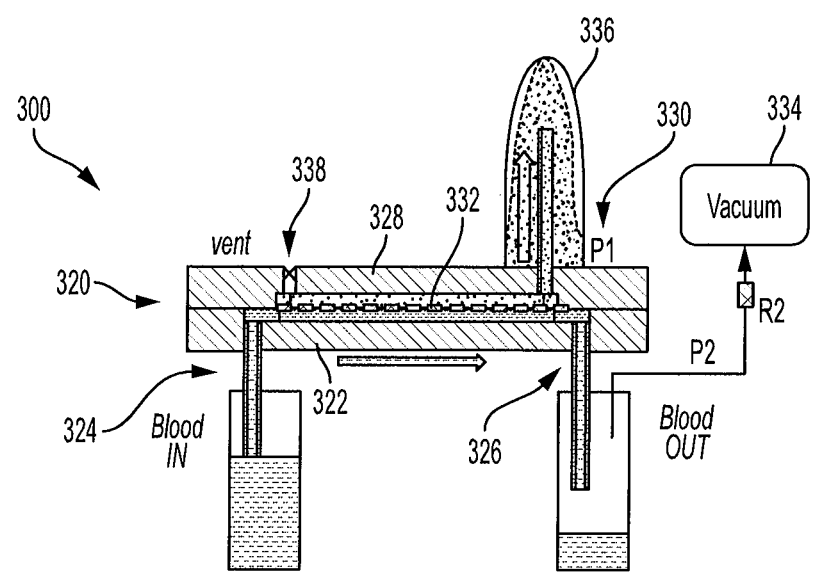
FIG. 13 is a schematic representation of a blood separation device in accordance with another embodiment of the present invention.
Figure 14:
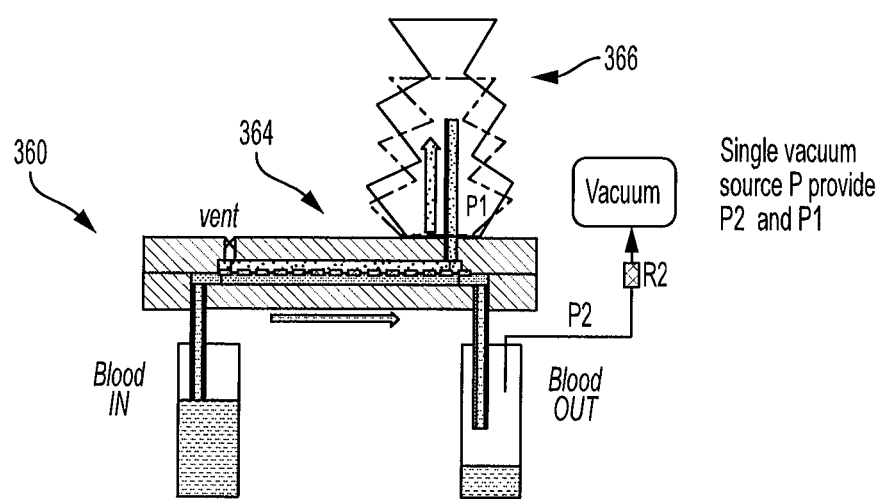
FIG. 14 is a schematic representation of a blood separation device in accordance with another embodiment of the present invention.
Figure 15:
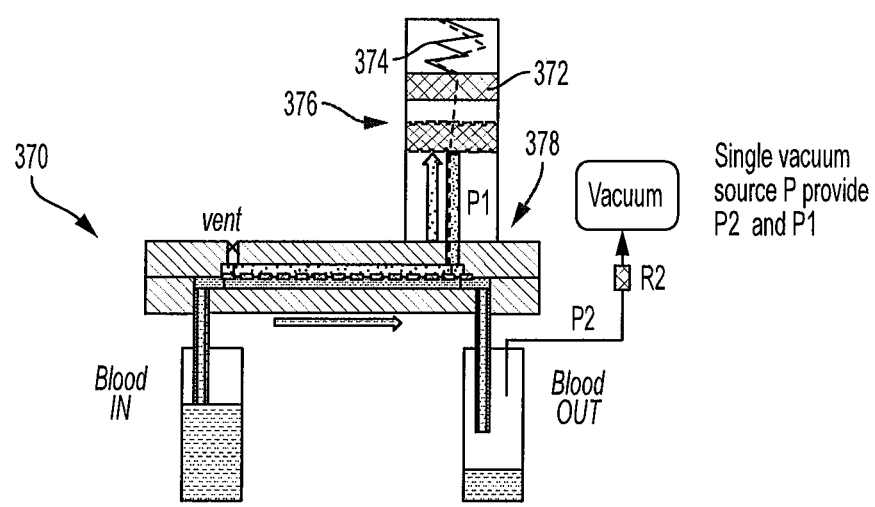
FIG. 15 is a schematic representation of a blood separation device in accordance with another embodiment of the present invention.

FIGS. 13-15 illustrate other exemplary embodiments of a blood separation device of the present disclosure. Referring to FIGS. 2 and 13, a blood separation device 300 of the present disclosure is adapted to receive a blood sample 12 having a whole blood portion 14 and a plasma portion 16. The present disclosure provides a blood separation device and a separation process that allows high quality plasma to be generated and a blood separation device that allows a single pressure source such as an evacuated tube to power the whole plasma separation process. The device design is simple, low cost and disposable. The plasma separation process is fast, easy to operate and produces high quality plasma samples from whole blood. It is scalable from sample size of micron liters to milliliters. The separation process does not require any hardware or electric power. It is operated by pressures which can be generated by using a syringe draw and/or an evacuated tube. The quality of the separated plasma is comparable to that of tube plasma generated by centrifugation and suitable for various diagnostic needs.

In one embodiment, after collecting a blood sample, the blood separation device 300 is able to separate a plasma portion of the blood sample from the whole blood portion. In one embodiment, after separation, the blood separation device 300 is able to transfer the plasma portion of the blood sample to a point-of-care testing device.

In one embodiment, the blood separation device 300 allows a vacuum source, such as an evacuated tube or a syringe draw, to power the plasma separation process. In one embodiment, the vacuum source not only drives the blood flow tangentially along a separation member membrane surface, but also provides the trans-membrane pressure needed to allow plasma flow through the membrane. In one embodiment, the blood separation device 300 eliminates the need for a plasma vacuum line and separate flow resister to regulate the pressure for the plasma side. This is possible because the vacuum power from the evacuated tube can be transferred to the plasma side through the porous TEM instead. The percent of the vacuum power transferred to the plasma side is controlled by the total chamber volume of the plasma side including plasma chamber, plasma storage and connecting channels or tubings.

Referring to FIG. 13, a blood separation device 300 generally includes a housing 320, a first chamber or blood chamber 322, a first chamber inlet 324, a first chamber outlet 326, a second chamber or plasma chamber 328, a second chamber outlet 330, a separation member or membrane 332, an actuator 334, and a deformable plasma collection container 336.

In one embodiment, the housing 320 defines a first chamber 322 and a second chamber 328. The first chamber 322 is adapted to receive a blood sample 12. The first chamber 322 includes a first chamber inlet 324 and a first chamber outlet 326. The second chamber 328 includes a second chamber outlet 330. In one embodiment, the blood separation device 300 includes a separation member 332 that is disposed between the first chamber 322 and the second chamber 328.

The separation member 332 is adapted to trap the whole blood portion 14 in the first chamber 322 and allow the plasma portion 16 to pass through the separation member 332 and into the second chamber 328, as shown in FIG. 2.

In one embodiment, the separation member 332 comprises a track-etched membrane. In one embodiment, the track-etched membrane comprises a polycarbonate membrane with a pore size of 0.4 um and a pore density of $1.5 \times 10^8/cm^2$. In one embodiment, a separation member 332 includes a pore size from 0.2 to 1 um. In one embodiment, a separation member 332 is formed of a material that can be PC, PET, PP or other materials. In one embodiment, a separation member 332 is hydrophobic. In one embodiment, the pore density of a separation member 332 can be from $5 \times 10^5/cm^2$ to $1 \times 10^6/cm^2$. In one embodiment, the thickness of a separation member 332 can be from 8 to 100 um. In one embodiment, the water flow rate of a separation member 332 can be in the range of 2.5 to 300 mL/min/$cm^2$ through the separation member 332.

In other embodiments, the separation member 332 may be either hollow fiber membrane filters or flat membrane filters. Membrane filter pore size and porosity can be chosen to optimize separation of clean (i.e., red blood cell free, white blood cell free, and platelet free) plasma 16 in an efficient manner. In other embodiments, the separation member 332 may comprise any filter that is able to trap the whole blood portion 14 in the first chamber 322 and allow the plasma portion 16 to pass through the separation member 332 and into the second chamber 328.

In one embodiment, the blood separation device 300 includes a deformable plasma collection container 336 that is in communication with the second chamber outlet 330. The plasma collection container 336 is able to collect and store the separated plasma 16.

In one embodiment, the blood separation device 300 includes an actuator 334. In one embodiment, actuation of the actuator 334 draws a blood sample 12 into the first chamber 322 and the separation member 332 is adapted to allow the plasma portion 16 of the blood sample 12 to pass through the separation member 332 to the second chamber 328. In one embodiment, the separation member 332 is adapted to trap the whole blood portion 14 in the first chamber 322 and allow the plasma portion 16 to pass through the separation member 332 and into the second chamber 328.

In one embodiment, the blood separation device 300 includes a blood chamber 322, a plasma chamber 328, and a separation member 332 that is operated by a pressure source, e.g., an actuator 334, to drive the blood flow and plasma flow. In one embodiment, the actuator 334 is a vacuum source. In one embodiment, the actuator 334 is an evacuated tube. In one embodiment, the actuator 334 is a syringe.

The blood separation device 300 provides a system that requires only one pressure source to drive both blood and plasma sides of the device. In one embodiment, a single actuator provides a first pressure to a portion of the first chamber 322 and a second pressure to a portion of the second chamber 328. In one embodiment, the second pressure is regulated by a porosity of the separation member 332 and the deformable plasma collection container 336. Advantageously, the blood separation device 300 of the present disclosure allows a single pressure source to power the whole plasma separation process.

In one embodiment, the blood separation device 300 includes built-in resisters to regulate a first pressure and a second pressure. For example, in one embodiment, the blood separation device 300 includes a first resister R1 in communication with the first pressure, as shown in FIG. 4B, and a second resister R2 in communication with the second pressure. The resisters may be a porous polymeric disc with 1 micron meter pore size from Porax. The porous material can be in many forms such as fiber, sintered polymeric materials, porous metals or any other air permeable materials. Alternatively, it can also be a small tube or channel built on a device that resists air flow. The built-in resisters regulate the vacuum levels P1 and P2, as shown in FIG. 13, with P1 being regulated by membrane porosity and the deformable plasma collection chamber 336. By providing a flexible material for the deformable plasma collection chamber 336, the interior volume may be adjusted to regulate the vacuum in the deformable plasma collection container 336. Under conditions of high vacuum, the flexible material of the deformable plasma collection container 336 flexes inward and reduces the collection volume, as shown via the dashed line of FIG. 13. Once the vacuum inside reaches a predetermined threshold, the deformable plasma collection container 336 returns to its original non-deformed state, as shown in FIG. 13.

In one embodiment, the blood separation device 300 includes a vent 338 that is transitionable between an open position and a closed position.

Figure 13A:
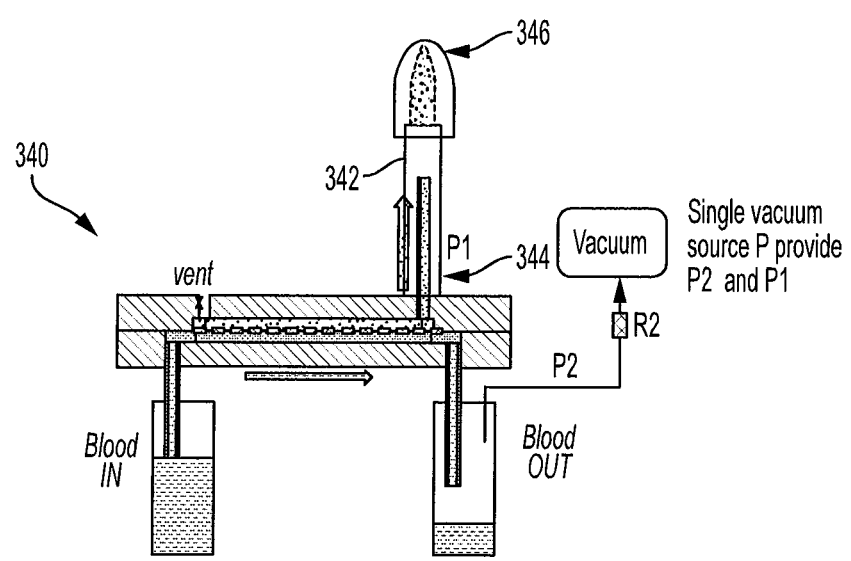
FIG. 13A is a schematic representation of a blood separation device in accordance with another embodiment of the present invention.

FIG. 13A illustrates another exemplary embodiment. The embodiment illustrated in FIG. 13A includes similar components to the embodiment illustrated in FIG. 13. For the sake of brevity, these similar components and the similar steps of using blood separation device 340 (FIG. 13A) will not all be discussed in conjunction with the embodiment illustrated in FIG. 13A.

Referring to FIG. 13A, in one embodiment, blood separation device 340 includes a rigid wall portion 342, a second chamber outlet 344, and a deformable plasma collection container 346. In one embodiment, the deformable plasma collection container 346 is in fluid communication with the second chamber outlet 344 via the rigid wall portion 342 as shown in FIG. 13A.

By providing a flexible material for the deformable plasma collection chamber 346, the interior volume may be adjusted to regulate the vacuum in the deformable plasma collection container 346. Under conditions of high vacuum, the flexible material of the deformable plasma collection container 346 flexes inward and reduces the collection volume, as shown via the dashed line of FIG. 13A. Once the vacuum inside reaches a predetermined threshold, the deformable plasma collection container 346 returns to its original non-deformed state, as shown in FIG. 13A.

Figure 13B:
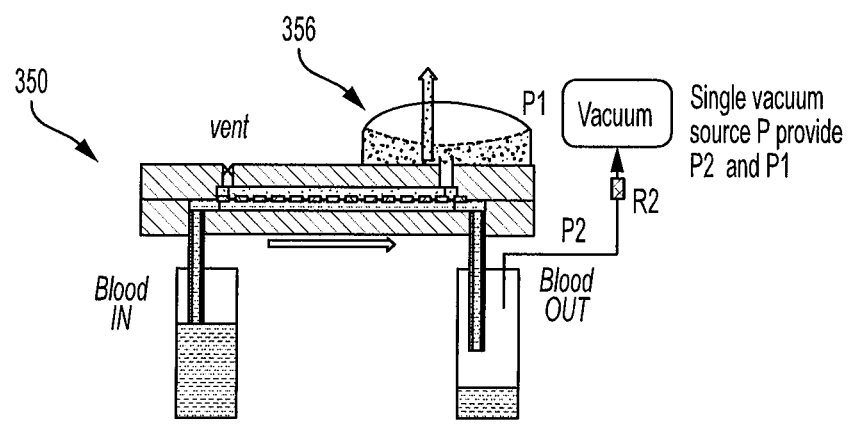
FIG. 13B is a schematic representation of a blood separation device in accordance with another embodiment of the present invention.

FIG. 13B illustrates another exemplary embodiment. The embodiment illustrated in FIG. 13B includes similar components to the embodiment illustrated in FIG. 13. For the sake of brevity, these similar components and the similar steps of using blood separation device 350 (FIG. 13B) will not all be discussed in conjunction with the embodiment illustrated in FIG. 13B.

Referring to FIG. 13B, in one embodiment, blood separation device 350 includes a deformable plasma collection container 356. In one embodiment, the deformable plasma collection container 356 has a domed shape.

By providing a flexible material for the deformable plasma collection chamber 356, the interior volume may be adjusted to regulate the vacuum in the deformable plasma collection container 356. Under conditions of high vacuum, the flexible material of the deformable plasma collection container 356 flexes inward and reduces the collection volume, as shown via the dashed line of FIG. 13B. Once the vacuum inside reaches a predetermined threshold, the deformable plasma collection container 356 returns to its original non-deformed state, as shown in FIG. 13B.

FIG. 14 illustrates another exemplary embodiment. The embodiment illustrated in FIG. 14 includes similar components to the embodiment illustrated in FIG. 13. For the sake of brevity, these similar components and the similar steps of using blood separation device 360 (FIG. 14) will not all be discussed in conjunction with the embodiment illustrated in FIG. 14.

Referring to FIG. 14, in one embodiment, the blood separation device 360 includes a deformable plasma collection container 366 that is in communication with the second chamber outlet 364. The plasma collection container 366 is able to collect and store the separated plasma 16. In one embodiment, the plasma collection container 366 comprises a flexible design such as a corrugated structure as shown in FIG. 14.

By providing a flexible design for the deformable plasma collection chamber 366, the interior volume may be adjusted to regulate the vacuum in the deformable plasma collection container 366. Under conditions of high vacuum, the flexible design of the deformable plasma collection container 366 collapses downward and reduces the collection volume, as shown via the dashed line of FIG. 14. Once the vacuum inside reaches a predetermined threshold, the deformable plasma collection container 366 returns to its original state, as shown in FIG. 14.

FIG. 15 illustrates another exemplary embodiment. The embodiment illustrated in FIG. 15 includes similar components to the embodiment illustrated in FIG. 13. For the sake of brevity, these similar components and the similar steps of using blood separation device 370 (FIG. 15) will not all be discussed in conjunction with the embodiment illustrated in FIG. 15.

Referring to FIG. 15, in one embodiment, the blood separation device 370 includes a plasma collection container 376 that is in communication with the second chamber outlet 378. The plasma collection container 376 is able to collect and store the separated plasma 16. In one embodiment, the blood separation device 370 includes a stopper or gasket 372 and a spring 374 contained within the plasma collection container 376. The stopper 372 and spring 374 provide a flexible design for the plasma collection container 376. In another embodiment, the flexible design may include an elastomer string.

By providing a flexible design for the plasma collection chamber 376, the interior volume may be adjusted to regulate the vacuum in the plasma collection container 376. Under conditions of high vacuum, the spring 374 within the plasma collection container 366 extends and moves the stopper 372 downward to a lower position and reduces the collection volume, as shown via the dashed lines of the spring 374 and the stopper 372 in FIG. 15. Once the vacuum inside reaches a predetermined threshold, the spring 374 and the stopper 372 return to their original positions, as shown in FIG. 15. With the stopper 372 in its original higher position, the interior volume of the plasma collection chamber 376 is increased.

Figure 16:
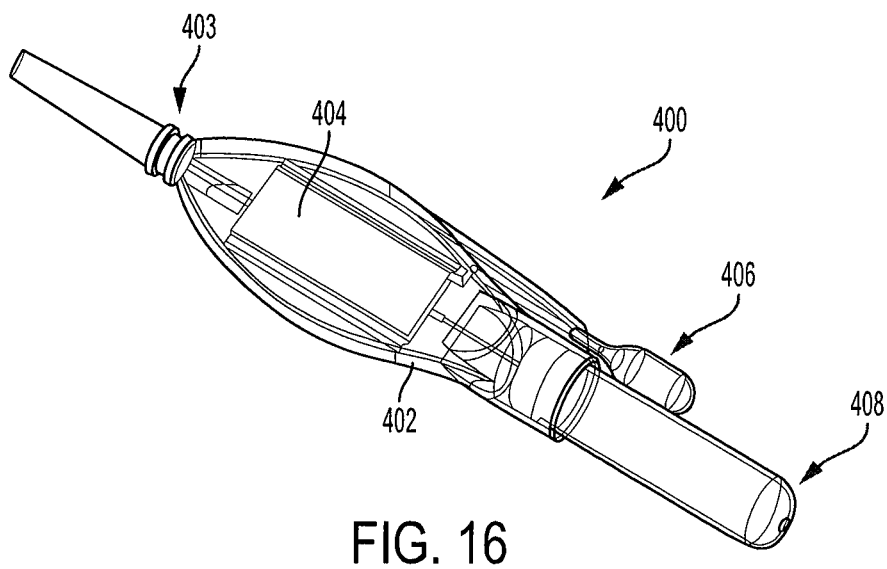
FIG. 16 is a perspective view of a blood separation device in accordance with another embodiment of the present invention.

Referring to FIG. 16, in one embodiment, a blood separation device 400 includes a housing 402, a male slip luer 403, a plasma separation membrane 404, a plasma dispense portion 406, and an evacuated tube 408 that powers blood draw and plasma separation.

Figure 17:
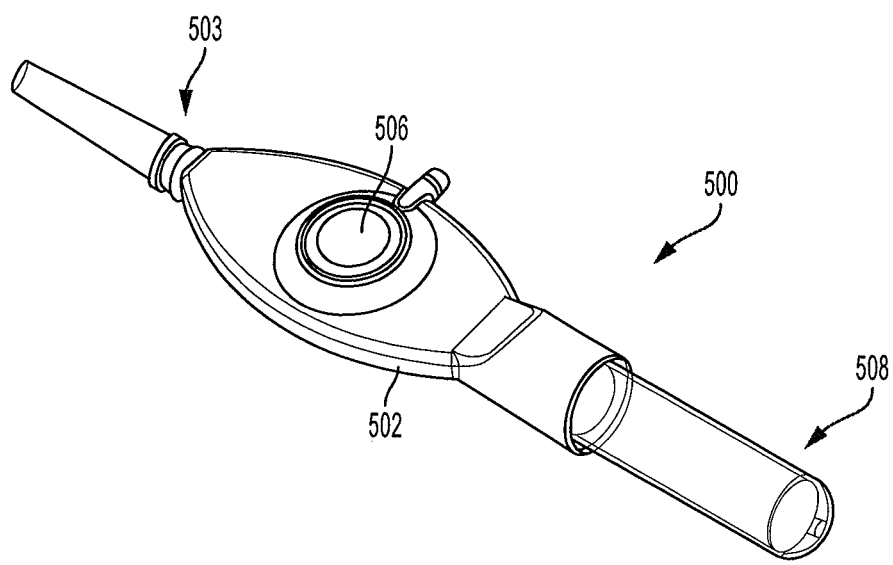
FIG. 17 is a perspective view of a blood separation device in accordance with another embodiment of the present invention.

Referring to FIG. 17, in one embodiment, a blood separation device 500 includes a housing 502, a male slip luer 503, a plasma separation membrane, a plasma dispense button 506, and an evacuated tube 508 that powers blood draw and plasma separation.

It is an advantage of the present invention that a sufficient volume of plasma can be filtered from whole blood with low risk of hemolysis in a fast processing time by using appropriate microchannel dimensions, flow conditions, and membrane dimensions.

In one embodiment, the cross-flow filtration process can generate sufficient plasma volume without membrane pore clogging if operation times are short and if the flow conditions produce sufficient shear forces as compared to the transmembrane pressure. It is contemplated herein that the combination of specific channel dimensions, flow conditions, and membrane dimensions would yield sufficient plasma under the desired time of operation with low hemolysis risk.

It is noted that previous attempts to leverage track-etch filtration took much longer to generate sufficient plasma or would require running the same sample of blood over the filtration membrane multiple instances. An embodiment of the present disclosure includes a device having dimensions and flow conditions that work for fresh blood to continuously pass over the membrane for less than three minutes. Moreover, sufficient plasma can be generated using the same filtration technology with different levels of hematocrit for undiluted blood.

Previous cross-flow filtration devices used a collection of small width channels under slow flow rates. The narrow channels required low flow rates to not cause hemolysis but then suffered from low plasma volumes being generated through the filtration membrane and also had sufficient cake layer build up over time. In one configuration, making the microchannel a single, larger width channel with smaller height, allows for flow conditions that drastically increase plasma volume with low risk of hemolysis can be achieved.

In one embodiment, a blood separation device of the present disclosure includes a larger width channel that allows for flows with higher flow rates and shear rates along the filtration membrane that do not cause hemolysis. In one embodiment of a blood separation device of the present disclosure, the plasma volume yield through the filtration membrane is enhanced by a channel with a shorter height and larger length and faster flow across the membrane.

Figure 21:
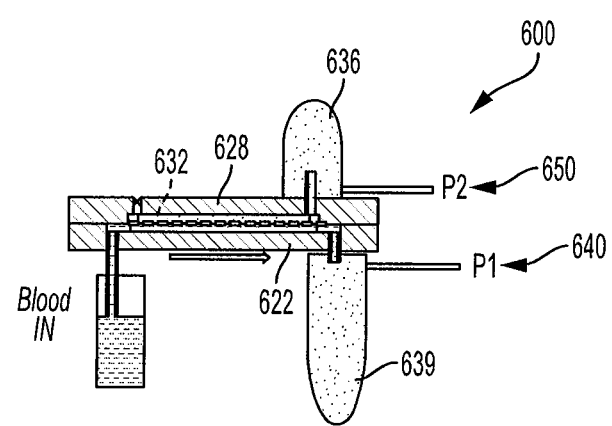
FIG. 21 is a schematic representation of a blood separation device in accordance with another embodiment of the present invention.

FIGS. 21-25 illustrate another exemplary embodiment of a blood separation device of the present disclosure and an exemplary plasma separation experiment of the present disclosure. Referring to FIGS. 2 and 21, a blood separation device 600 of the present disclosure is adapted to receive a blood sample 12 having a whole blood portion 14 and a plasma portion 16. The present disclosure provides a blood separation device and a separation process that allows high quality plasma to be generated and a blood separation device that allows a single pressure source such as an evacuated tube to power the whole plasma separation process. The device design is simple, low cost and disposable. The plasma separation process is fast, easy to operate and produces high quality plasma samples from whole blood. It is scalable from sample size of micron liters to milliliters. The separation process does not require any hardware or electric power. It is operated by pressures which can be generated by using a syringe draw and/or an evacuated tube. The quality of the separated plasma is comparable to that of tube plasma generated by centrifugation and suitable for various diagnostic needs.

In one embodiment, after collecting a blood sample, the blood separation device 600 is able to separate a plasma portion of the blood sample from the whole blood portion. In one embodiment, after separation, the blood separation device 600 is able to transfer the plasma portion of the blood sample to a point-of-care testing device.

Referring to FIG. 21, in one embodiment, a blood separation device 600 includes a blood chamber 622 and a plasma chamber 628, connected through a separation membrane 632, a plasma collection container 636, and a blood collection container 639. In one embodiment, the separation membrane 632 has a pore size of 0.4 um and the membrane 632 is a PCTE membrane.

Both containers 636, 639 are connected to their respective independent vacuum sources 640, 650 to respectively supply constant vacuums P1 and P2. The volume of the containers 636, 639 is large enough to collect the plasma sample and the waste blood sample. The pressure inside the collection containers 636, 639 is constant throughout the plasma separation process. The blood chamber 622 has a size of 50 mm×10 mm×0.08 mm and the plasma chamber 628 has a size of 40 mm×10 mm×0.08 mm. The plasma chamber 628 has ridges to support the membrane 632.

An exemplary experiment of the present disclosure uses two independent pressures P1 and P2 to understand their impact on plasma separation performance. Input blood volume is 3 mL whole blood of 38-42% hematocrit. And the pressure P1 and P2 settings are from 1 to 9 psi.

Figure 23:
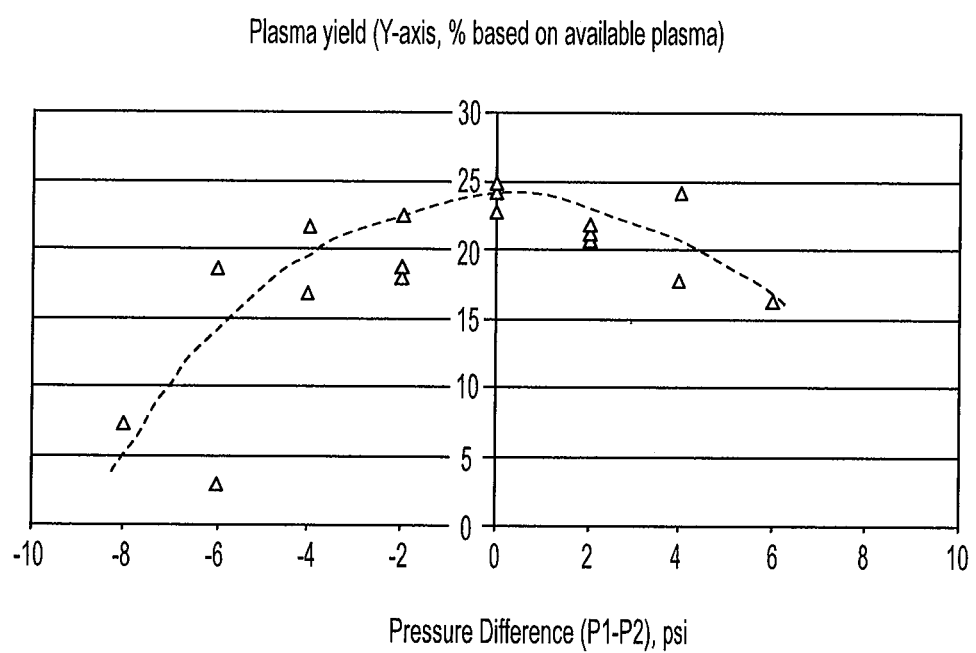
FIG. 23 is a graph illustrating plasma yield vs. pressure difference of a method and device of yielding plasma in accordance with an embodiment of the present invention.
Figure 24:
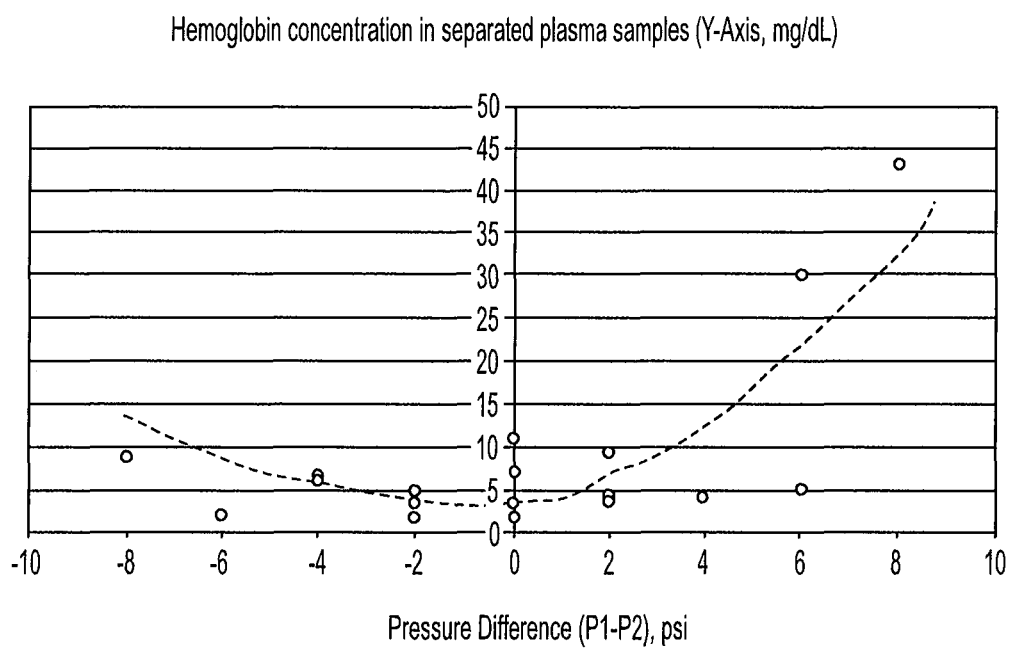
FIG. 24 is a graph illustrating hemoglobin in plasma vs. pressure difference of a method and device of yielding plasma in accordance with an embodiment of the present invention.
Figure 25:
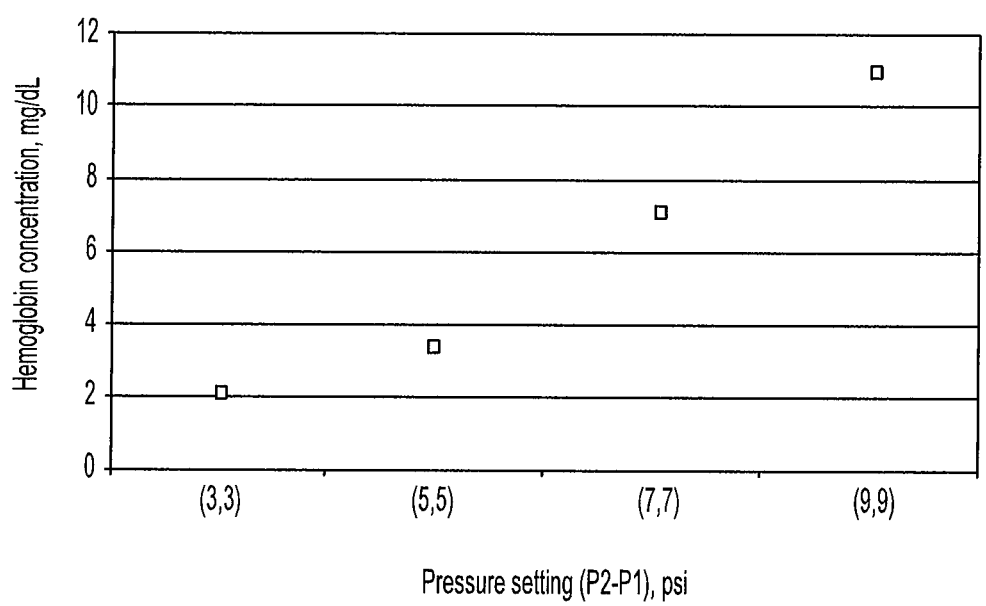
FIG. 25 is a graph illustrating hemoglobin vs. pressure setting of a method and device of yielding plasma in accordance with an embodiment of the present invention.

P1 and P2 were kept constant at the experiment settings shown in the Table of FIG. 22. Referring to FIGS. 23-25, plasma yield, hemoglobin in plasma and separation time were determined. Each data point in the Table of FIG. 22 is an average of three independent device tests. When the difference is large between the pressure settings P1 and P2, the system was difficult to keep the selected pressure settings due to the cross talk through the membrane at the beginning of the experiment.

Referring to FIG. 23, when the plasma yield is plotted against pressure differential (P2-P1), a trend is observed that the plasma yield reaches a maximum when pressure P1 and P2 are close to each other. The device, however, is functional in a wider range of pressure from 3 to 9 psi. Referring to FIGS. 24 and 25, a similar observation was made for hemoglobin concentration in plasma. The device causes minimum hemolysis when the pressure settings (P1 and P2) are similar and the pressures are small.

It is noted herein that plasma generated using this invention contains diagnostically relevant analytes. Examples of analytes that can be tested directly from plasma separated using this technology include, but are not limited to those in general chemistry panels (e.g. potassium, sodium, calcium, magnesium, chloride, phosphate), triglycerides, cholesterol, high density lipoprotein (HDL)-cholesterol, low density lipoprotein (LDL)-cholesterol, C-reactive protein (CRP), aspartate transaminase/glutamic-oxaloacetic transaminase (AST/GOT), lipase, albumin, bilirubin, glucose, creatinine, IgG, ferritine, insulin, rheumatoid factors and prostate-specific antigen (PSA); hormones such as thyroid-stimulating hormone (TSH), free T3 Total T3, Free T4, Total T4, follicle-stimulating hormone (FSH) and beta human chorionic gondatropin (hCG); vitamins such as Vitamin D and Vitomin B12; and cardiac markers such as Troponin (cTnI, cTnT), b-type-natriuretic-peptide (BNP), NTproBNP, D-dimer, creatine kinase (CK), CK-MB, myoglobin. Additional analytes that can be tested from plasma separated using this technology include, but are not limited to nucleic acids (e.g. circulating cell-free DNA, microRNAs), exosomes, DNA viruses (e.g. Hepatitis-B) and RNA viruses (e.g. HIV).

Figure 26:
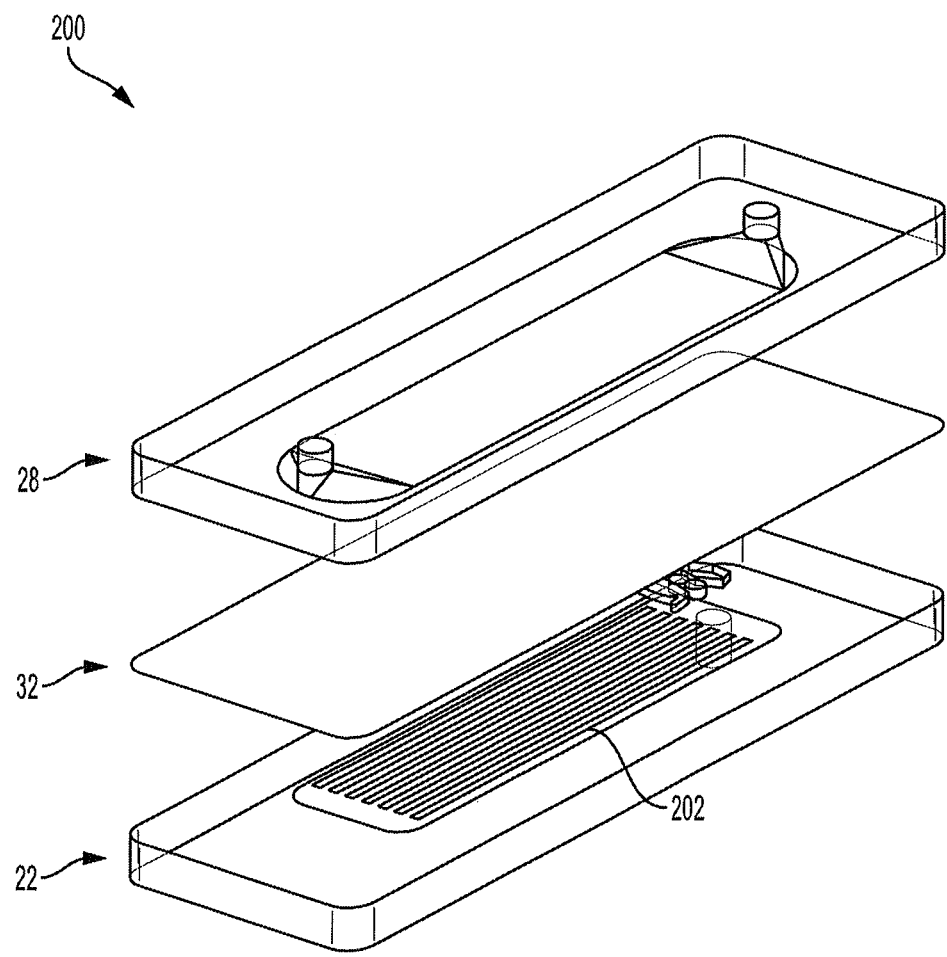
FIG. 26 is an exploded, perspective view of a blood separation microfluidic chip in accordance with another embodiment of the present invention.
Figure 27:
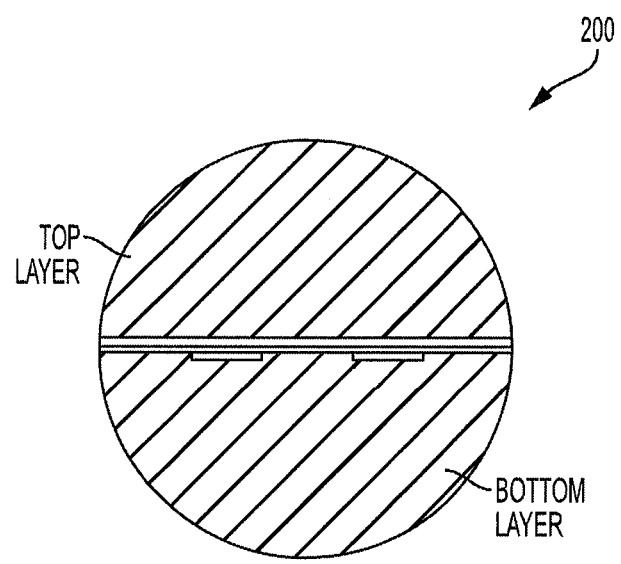
FIG. 27 is a cross-sectional view of a blood separation microfluidic chip in accordance with another embodiment of the present invention.

Referring to FIGS. 26 and 27, in one embodiment, a blood separation device of the present disclosure comprises a microfluidic chip 200. The microfluidic chip 200 includes a first chamber 22, a second chamber 28, and a separation member 32 that is disposed between the first chamber 22 and the second chamber 28.

In one embodiment, the first chamber 22 has a height of approximately 65-95 µm for optimum separation of plasma. In one embodiment, the first chamber 22 includes supporting ribs 202. In one embodiment, the supporting ribs 202 have a height of approximately 65-95 µm. In one embodiment, the first chamber 22 has a height of approximately 70-90 µm for optimum separation of plasma. In one embodiment, the supporting ribs 202 have a height of approximately 70-90 µm. In one embodiment, the first chamber 22 has a height of approximately 75-85 µm for optimum separation of plasma. In one embodiment, the supporting ribs 202 have a height of approximately 75-85 µm. In one embodiment, the first chamber 22 has a height of approximately 80 µm for optimum separation of plasma. In one embodiment, the supporting ribs 202 have a height of approximately 80 µm.

In one embodiment, the second chamber 28 has a height of approximately 65-95 µm for optimum separation of plasma. In one embodiment, the second chamber 28 has a height of approximately 70-90 µm for optimum separation of plasma. In one embodiment, the second chamber 28 has a height of approximately 75-85 µm for optimum separation of plasma. In one embodiment, the second chamber 28 has a height of approximately 80 µm for optimum separation of plasma.

In one embodiment, the separation member 32 has a thickness of approximately 9-15 µm for optimum separation of plasma. In one embodiment, the separation member 32 has a thickness of approximately 10-14 µm for optimum separation of plasma. In one embodiment, the separation member 32 has a thickness of approximately 11-13 µm for optimum separation of plasma. In one embodiment, the separation member 32 has a thickness of approximately 12 µm for optimum separation of plasma.

In one embodiment, the separation member 32 has a pore size of 0.4 µm. In one embodiment, the separation member 32 is treated with a water soluble chemical solution.

A blood separation device and a separation process of the present disclosure allows high quality plasma to be generated in less than 1 minute and the blood separation device allows a single pressure source such as a vacutainer tube to power the whole plasma separation process. The device design is simple, low cost and disposable. The plasma separation process is fast, easy to operate and produces high quality plasma samples from whole blood. It is scalable from sample size of micron liters to milliliters. The separation process does not require any hardware or electric power. It is operated by pressures which can be generated by using a syringe draw and/or a vacutainer tube. The quality of the separated plasma is comparable to that of tube plasma generated by centrifugation and suitable for various diagnostic needs. The separation of plasma from whole blood using a blood separation device of the present disclosure that includes a track-etch membrane (TEM) is substantially faster than centrifugation methods.

The above-described qualities of the present disclosure make the TEM approach of the present disclosure a promising sample preparation method for point-of-care assays using plasma. Experiments using a blood separation device of the present disclosure indicate excellent (low) bias for soluble analytes in TEM-separated plasma. Utilizing the results of these experiments of the present disclosure, a model HIV viral load (VL) assay was designed to measure the relative recovery of HIV RNA in plasma separated from spiked whole blood using the TEM approach of the present disclosure compared to plasma collected via centrifugation.

A description of the materials and methods of such experiments will now be described. Whole blood was collected by venipuncture from normal donors into EDTA (K2) Vacutainer® blood collection tubes. Vacutainer® blood collection tubes are commercially available from Becton, Dickinson and Company. A portion of the specimen was then spiked with replication-defective HIV-1 virus particles (AccuSpan HIV-1 Linearity Panel, SeraCare, Milford, Mass.) to a target concentration of $10^3$ or $10^5$ HIV genome equivalents (copies) per mL. Plasma was separated from replicate aliquots of spiked blood either by either centrifugation (1000× g, 20 min, 8° C.) or passage through TEM devices powered by 10 mL Vacutainer tubes. Separation time using TEM devices was <1 minute for each 3 mL aliquot of spiked whole blood.

A standard curve was formulated by serial dilution of the same HIV-1 stock into unspiked autologous plasma. RNA was purified from all plasma samples (centrifuged, TEM-separated, standards, and normal unspiked plasma) using the QIAamp® DSP Viral RNA Mini Kit, available from Qiagen®, run on an automated QIAcube® system or manually using a QIAvac manifold.

Quantitative RT-PCR reactions (20 µL total, including 7 µL purified RNA template) were set up in quadruplicate using EXPRESS One-Step Superscript® reagents available from Invitrogen™ of Life Technologies Corporation. HIV-1 primer and 5'-nuclease probe sequences and concentrations were based on a previously published configuration (Candotti, D., J. Temple, S. Owusu-Ofori, and J.-P. Allain. 2004. Multiplex real-time quantitative RT-PCR assay for hepatitis B virus, hepatitis C virus, and human immunodeficiency virus type 1. J. Virol. Methods 118, 39-47). Amplification with real-time fluorescence measurement was performed on a BioRad CFX96 Touch, and threshold cycle (Cq) values were determined using the packaged CFX Manager software (Hercules, Calif.). HIV-1 viral load (copies/mL) for each sample was calculated by interpolation against a semi-log plot fitted to the standard curve, followed by comparison and statistical analysis (Prism 6.0, GraphPad Software, La Jolla, Calif.) of viral loads present in centrifuged or TEM-separated plasma.

Figure 29:
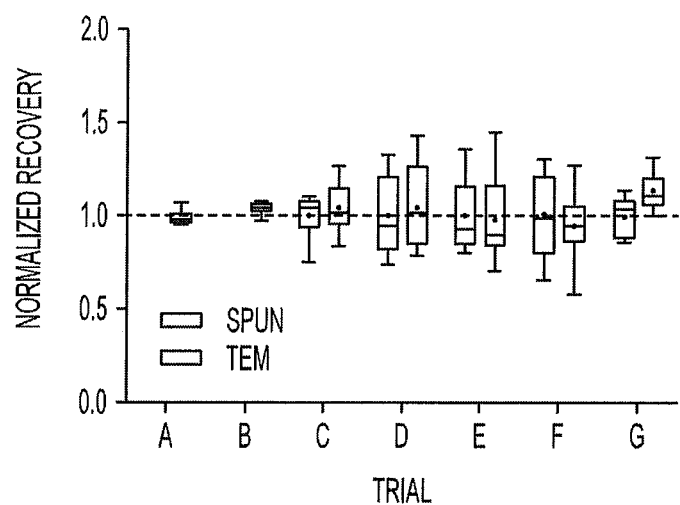
FIG. 29 is a graph illustrating normalized HIV recovery from plasma separated from spiked whole blood in accordance with an embodiment of the present invention.

A description of the results of such experiments will now be described. Seven trials were conducted on separate days; three targeted a spiked whole-blood [HIV] of $10^5$ copies/mL and four targeted $10^3$ copies/mL. Aggregated HIV VL data from all seven trials are shown in FIG. 18. A ratio-paired t test indicated no significant difference (P=0.3525) in same-day HIV VL means from spun or TEM-processed plasma. To further facilitate comparison across different days and concentrations, each daily data set was normalized by dividing the mean VL of each replicate by the same-day mean VL from centrifuged plasma replicates (FIG. 29). Again, no significant difference was found (P=0.3347) by unpaired t test comparing normalized HIV recovery in spun or TEM plasmas.

Figure 28:
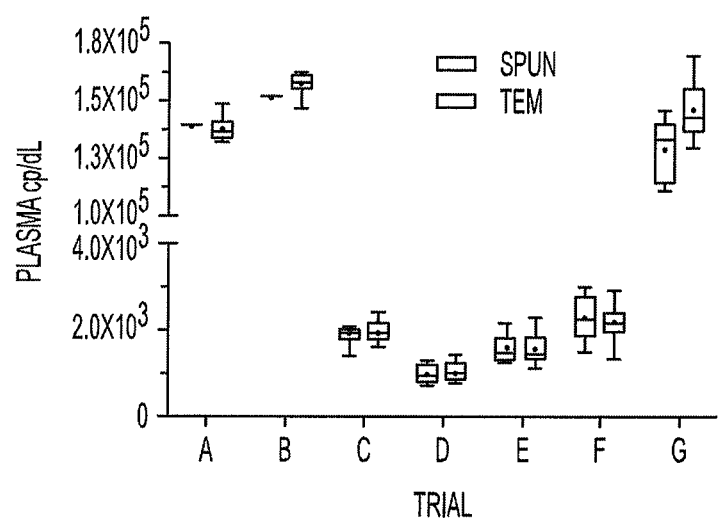
FIG. 28 is a graph illustrating recovery of HIV RNA from plasma processed by centrifugation or a track-etch membrane device in accordance with an embodiment of the present invention.

Referring to FIG. 28, recovery of HIV RNA from plasma processed by centrifugation or TEM device is shown. Trials A and B were conducted with a single spun sample and six TEM replicates. Trials C through G tested eight replicates each of spun and TEM plasma. Boxes and whiskers $25^{th}/75^{th}$ and $5^{th}/95^{th}$ percentiles, respectively; medians are marked by lines and means by (+).

Referring to FIG. 29, normalized HIV recovery from plasma separated from spiked whole blood is shown. Mean VL from TEM-processed plasma samples were divided by the mean VL across all available same-day replicates of centrifuged plasma.

This data indicates no significant HIV VL bias in TEM-separated plasma relative to the conventional centrifugation method at two clinically relevant [HIV] values ($10^3$ or $10^5$ copies per mL of whole blood). Thus, the speed advantage conferred by TEM plasma separation of the present disclosure (<1 minute) relative to conventional centrifugation (20 minutes) necessitates no apparent penalty in analyte recovery within a model HIV viral load assay.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A blood separation device comprising:
a housing defining a first chamber having a first chamber inlet and a first chamber outlet wherein the first chamber outlet is placed a lateral distance from the first chamber inlet, wherein the first chamber has a height of about 65 to about 95 µm,
a second chamber having a second chamber outlet, and including a separation member disposed between the first chamber and the second chamber thereby dividing the housing into the first and second chambers and defining a tangential flow path from the first chamber inlet to the first chamber outlet, wherein the first chamber is adapted to receive a blood sample through the first chamber inlet; and a single vacuum source actuator for a single vacuum source,
wherein the single vacuum source is applied adjacent the separation member by a first line to the first chamber outlet and draws the blood sample into the first chamber and along the tangential flow path defined by the separation member and wherein the single vacuum source is the only vacuum source in the blood separation device, wherein the separation member is adapted to allow a plasma portion of the blood sample to pass through the separation member into the second chamber.

2. The blood separation device of claim 1, wherein the separation member is adapted to trap a whole blood portion of the blood sample in the first chamber and allow the plasma portion to pass through the separation member and into the second chamber.

3. The blood separation device of claim 1, further comprising a plasma collection container in communication with the second chamber outlet.

4. The blood separation device of claim 1, wherein the single vacuum source actuator provides a first pressure to a portion of the first chamber via the first line.

5. The blood separation device of claim 4, wherein a second pressure in the second chamber is regulated by a porosity of the separation member and a volume of the second chamber.

6. The blood separation device of claim 1, wherein the single vacuum source actuator is an evacuated tube.

7. The blood separation device of claim 1, wherein the separation member comprises a track-etched membrane.

8. The blood separation device of claim 1, further comprising a vent transitionable between an open position and a closed position.

9. The blood separation device of claim 1 wherein the separation member has a pore size of 0.2 µm to 1 µm.

10. The blood separation device of claim 1 wherein the pressure difference between the outlet of the first chamber and the outlet of the second chamber is in the range of 8 psi to −8 psi.

11. The blood separation device of claim 10 wherein the separation member has a pore size of 0.2 µm to 1 µm.

12. The blood separation device of claim 1 wherein the first chamber height is 80 µm, the first chamber width is 10 mm and the first chamber length is 50 mm.

13. A blood separation device comprising: a housing defining a first chamber having a first chamber inlet and a first chamber outlet wherein the first chamber outlet is placed a lateral distance from the first chamber inlet and wherein the first chamber has a height of about 65 to about 95 µm, a second chamber having a second chamber outlet, and including a separation member disposed between the first chamber and the second chamber thereby dividing the housing into the first and second chambers and defining a tangential flow path between the first chamber inlet and the first chamber outlet, wherein the first chamber is adapted to receive a blood sample through the first chamber inlet; a single vacuum source actuator in communication with a portion of the first chamber wherein the single vacuum source is the only vacuum source in the blood separation device; and a plasma collection container in communication with the second chamber outlet, wherein the single vacuum source actuator draws the blood sample into the first chamber by a first line and along the tangential flow path to the first chamber outlet and the separation member is adapted to allow a plasma portion of the blood sample to pass through the separation member to the second chamber.

14. The blood separation device of claim 13, wherein the single vacuum source actuator provides a first pressure to a portion of the first chamber and a second pressure to a portion of the second chamber.

15. The blood separation device of claim 14, wherein the second pressure is regulated by a porosity of the separation member and the plasma collection container.

16. The blood separation device of claim 14, further comprising a first resister in communication with the first pressure.

17. The blood separation device of claim 14, further comprising a second resister in communication with the second pressure.

18. The blood separation device of claim 13, wherein the separation member is adapted to trap a whole blood portion of the blood sample in the first chamber and allow the plasma portion to pass through the separation member and into the second chamber.

19. The blood separation device of claim 13, wherein the single vacuum source actuator is a syringe draw.

20. The blood separation device of claim 13, wherein the single vacuum source actuator is an evacuated tube.

21. The blood separation device of claim 13, wherein the separation member comprises a track-etched membrane.

22. The blood separation device of claim 13, further comprising a vent transitionable between an open position and a closed position.

23. The blood separation device of claim 13 wherein the separation member has a pore size of 0.2 μm to 1 μm.

24. The blood separation device of claim 13 wherein the pressure difference between the outlet of the first chamber and the outlet of the second chamber is in the range of 8 psi to −8 psi.

25. The blood separation device of claim 24 wherein the separation member has a pore size of 0.2 μm to 1 μm.

26. The blood separation device of claim 13 wherein the first chamber height is 80 μm, the first chamber width is 10 mm and the first chamber length is 50 mm.

27. A blood separation device comprising: a housing defining a first chamber having a first chamber inlet and a first chamber outlet wherein the first chamber outlet is placed a lateral distance from the first chamber inlet wherein the first chamber has a height of about 65 to about 95 μm, a second chamber having a second chamber outlet, and including a separation member disposed between the first chamber and the second chamber thereby dividing the housing into the first and second chambers and wherein the separation member defines a tangential flow path between the first chamber inlet to the first chamber outlet, wherein the first chamber is adapted to receive a blood sample through the first chamber inlet; an actuator in communication with a portion of the first chamber; and a plasma collection container in communication with the second chamber outlet, wherein actuation of the actuator draws the blood sample into the first chamber and the separation member is adapted to allow a plasma portion of the blood sample to pass through the separation member to the second chamber, and wherein the actuator provides a single pressure source that is directed only to a side of the first chamber wherein the single pressure source is the only pressure source in the blood separation device wherein the pressure source draws the blood sample along the tangential flow path defined by the separation member, with a volume of a side of the second chamber configured to control a ratio of pressure between the side of the first chamber and the side of the second chamber.

28. The blood separation device of claim 27 wherein the plasma collection container has a volume selected to provide a target plasma yield.

29. The blood separation device of claim 27 wherein the separation member has a pore size of 0.2 μm to 1 μm.

30. The blood separation device of claim 27 wherein the pressure difference between the outlet of the first chamber and the outlet of the second chamber is in the range of 8 psi to −8 psi.

31. The blood separation device of claim 30 wherein the separation member has a pore size of 0.2 μm to 1 μm.

32. The blood separation device of claim 27 wherein the first chamber height is 80 μm, the first chamber width is 10 mm and the first chamber length is 50 mm.

* * * * *